(12) United States Patent
Novotni et al.

(10) Patent No.: US 9,987,446 B2
(45) Date of Patent: Jun. 5, 2018

(54) SYSTEM FOR AUTOMATED ADJUSTMENT OF A PRESSURE SET BY A RESPIRATION DEVICE

(71) Applicant: Hamilton Medical AG, Bonaduz (CH)

(72) Inventors: Dominik Novotni, Chur (CH); Thomas Laubscher, Rhaezuens (CH)

(73) Assignee: HAMILTON MEDICAL AG, Bonaduz (CH)

( * ) Notice: Subject to any disclaimer, the term of this patent is extended or adjusted under 35 U.S.C. 154(b) by 440 days.

(21) Appl. No.: 14/770,428

(22) PCT Filed: Feb. 10, 2014

(86) PCT No.: PCT/EP2014/052529
§ 371 (c)(1),
(2) Date: Aug. 25, 2015

(87) PCT Pub. No.: WO2014/131605
PCT Pub. Date: Sep. 4, 2014

(65) Prior Publication Data
US 2016/0008561 A1    Jan. 14, 2016

(30) Foreign Application Priority Data
Feb. 26, 2013   (DE) .................. 10 2013 203 177

(51) Int. Cl.
*A61M 16/00*   (2006.01)
*A61B 5/053*   (2006.01)
*A61B 5/08*    (2006.01)

(52) U.S. Cl.
CPC ....... *A61M 16/0069* (2014.02); *A61B 5/0536* (2013.01); *A61B 5/0809* (2013.01);
(Continued)

(58) Field of Classification Search
CPC .......... A61M 16/0051; A61M 16/0069; A61M 2016/0027; A61M 2205/50;
(Continued)

(56) References Cited

U.S. PATENT DOCUMENTS

| 4,630,614 A | * | 12/1986 | Atlas | ............... A61B 5/0816 600/534 |
| 6,501,198 B2 | | 12/2002 | Taylor et al. | |

(Continued)

FOREIGN PATENT DOCUMENTS

| DE | 103 01 202 B3 | 1/2004 |
| EP | 1 593 341 B1 | 2/2010 |
| JP | 2003-534867 A | 11/2003 |

OTHER PUBLICATIONS

Mouloud A. Denaï et al., "Absolute Electrical Impedance Tomography (aEIT) Guided Ventilation Therapy in Critical Care Patients: Simulations and Future Trends", IEEE Transactions on Information Technology in Biomedicine, vol. 14, No. 3, May 2010, pp. 641-649.

(Continued)

*Primary Examiner* — Joshua Lee
(74) *Attorney, Agent, or Firm* — Seed Intellectual Property Law Group LLP

(57) ABSTRACT

There is suggested a system for automated adjustment of a pressure set by a respiration device, in particular a positive end-expiratory pressure and/or a maximum airway pressure, comprising: an arrangement for electrical impedance tomography for detecting an electrical impedance distribution along at least a two-dimensional cross-section through the human thorax at least at the end of an inspiration phase and at the end of an associated expiration phase; a device for dividing the detected electrical impedance distribution at the end of the inspiration phase and at the end of the expiration phase into a plurality of EIT pixels and for determining a value of the electrical impedance at the end of the inspiration (Continued)

phase and at the end of the expiration phase, as associated with a respective EIT pixel; and a device for automated adjustment of the pressure set by the respiration device on the basis of a comparison (i) of a deviation between the value of the electrical impedance at the end of the inspiration phase associated with an individual EIT pixel and the value of the electrical impedance at the end of the expiration phase associated with the respective individual EIT pixel (ii) with a deviation between the value of the electrical impedance at the end of the inspiration phase and the value of the electrical impedance at the end of the expiration phase, as determined on the basis of the entirety of EIT pixels.

25 Claims, 10 Drawing Sheets

(52) U.S. Cl.
CPC . *A61M 16/0051* (2013.01); *A61M 2016/0027* (2013.01); *A61M 2205/3303* (2013.01); *A61M 2205/50* (2013.01); *A61M 2205/502* (2013.01); *A61M 2230/08* (2013.01); *A61M 2230/42* (2013.01); *A61M 2230/65* (2013.01)

(58) Field of Classification Search
CPC .... A61M 2205/502; A61M 2205/3303; A61M 2230/08; A61M 2230/42; A61M 2230/65; A61B 5/0536; A61B 5/0809
See application file for complete search history.

(56) References Cited

U.S. PATENT DOCUMENTS

| | | | |
|---|---|---|---|
| 6,502,984 B2 | 1/2003 | Ogura et al. | |
| 7,435,226 B2* | 10/2008 | Suarez | A61B 5/0536 600/529 |
| 2006/0260611 A1* | 11/2006 | Garber | A61B 5/0536 128/204.23 |
| 2007/0246046 A1* | 10/2007 | Teschner | A61B 5/0536 128/204.23 |
| 2010/0228143 A1 | 9/2010 | Teschner et al. | |
| 2013/0002264 A1* | 1/2013 | Garber | A61B 5/0536 324/600 |
| 2013/0123617 A1* | 5/2013 | Sola i Caros | A61B 5/02125 600/427 |
| 2013/0190577 A1* | 7/2013 | Brunner | A61B 5/0536 600/301 |
| 2014/0221806 A1* | 8/2014 | Garber | A61B 5/0809 600/382 |
| 2014/0221864 A1* | 8/2014 | Garber | A61B 5/0536 600/533 |
| 2014/0221865 A1* | 8/2014 | Garber | A61B 5/7239 600/533 |

OTHER PUBLICATIONS

The Acute Respiratory Distress Syndrome Network, "Ventilation With Lower Tidal Volumes as Compared With Traditional Tidal Volumes for Acute Lung Injury and the Acute Respiratory Distress Syndrome," The New England Journal of Medicine, 2000, 342: pp. 1301-1308.
Bikker et al., "Bedside measurement of changes in lung impedance to monitor alveolar ventilation in dependent and non-dependent parts by electrical impedance tomography during a positive end-expiratory pressure trial in mechanically ventilated intensive care unit patients," Critical Care, 2010, 14(3), R100, 9 pages.
Brochard L., "What is a pressure-volume curve?" Critical Care, 2006, 10: pp. 156-158.
Grasso et al., "ARDSnet Ventilatory Protocol and Alveolar Hyper-inflation," American Journal of Respiratory Critical Care Medicine, 2007, 176: pp. 761-767.
Victorino et al., "Imbalances in Regional Lung Ventilation—A Validation Study on Electrical Impedance Tomography," American Journal of Respiratory and Critical Care Medicine, 2004, 169(7), pp. 791-800.

* cited by examiner

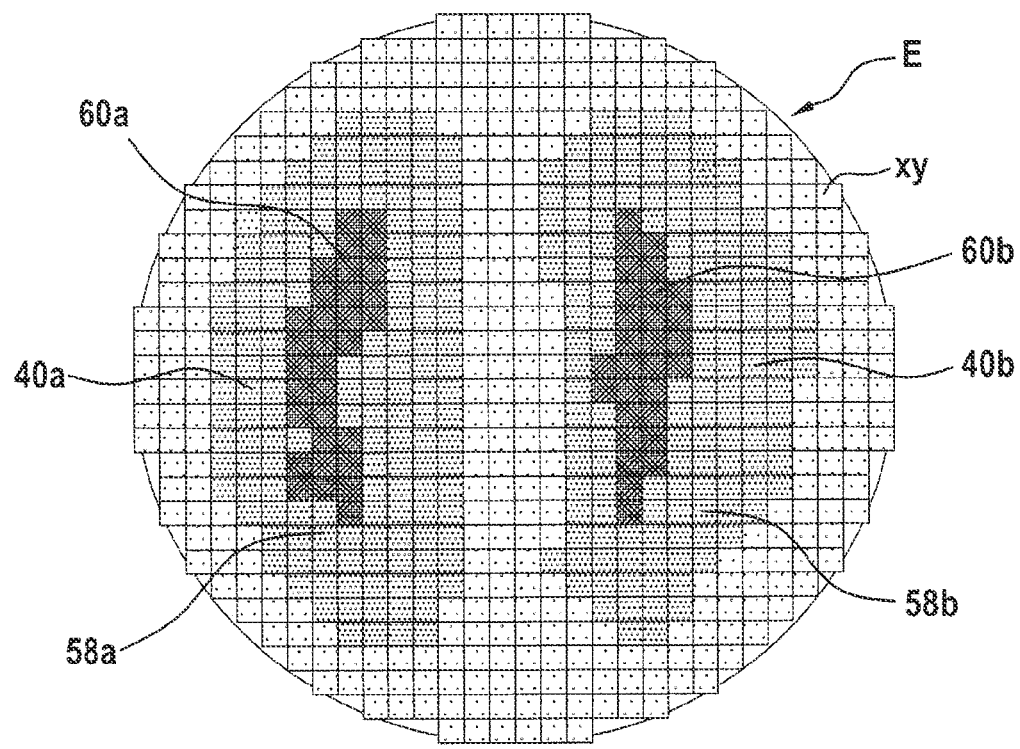

SYSTEM FOR AUTOMATED ADJUSTMENT OF A PRESSURE SET BY A RESPIRATION DEVICE

BACKGROUND

Technical Field

The present invention relates to a system for the automated adjustment of a pressure specified or set by a respiration device, in particular a positive end-expiratory pressure and/or a maximum airway pressure. The invention also relates to a device for machine respiration that is provided with such a system for adjusting the set pressure, in particular the positive end-expiratory pressure and/or the maximum airway pressure.

Description of the Related Art

In today's common forms of machine respiration, breathing gas is supplied to the patient at a positive pressure. This is why the airway pressure or the alveolar pressure during respiration is greater than the pressure in the pleural gap surrounding the pulmonary alveoli at least during the inspiration phase. During the expiration phase, there is no pressure applied to the airway by the respiration device, with the result that the lung tissue relaxes and the airway pressure or alveolar pressure drops. This kind of positive pressure respiration may under certain circumstances have the effect that the pressure conditions in the respiratory tract and in the alveoli, respectively, at the end of the expiration phase become so unfavorable that there is a collapse of parts of the alveoli. The collapsed part of the lung volume then will have to be unfolded anew in the subsequent breathing cycle. The functional residual capacity of the lungs is severely compromised, so that the oxygen saturation decreases, and also the lung tissue is permanently damaged.

In order to prevent a collapse of alveoli at the end of the expiration phase, positive-pressure machine respiration usually is carried out using a so-called positive end-expiratory pressure, which usually is briefly referred to as PEEP. With this measure it is in many cases possible to achieve an improvement in oxygen saturation.

In respiration with PEEP, the respiration device permanently applies—that is, both during the inspiration phase and during the expiration phase—a predetermined positive pressure, the PEEP, to the airway. Thus, the PEEP is still applied also after the end of the expiration phase. The maximum airway pressure is applied at the end of the inspiration phase when the airway is subjected to the highest load by the respiration device.

Ideally, the PEEP should be set large enough so that, during the expiration phase, the alveolar pressure is not, or at least only so far, below the pressure in the pleural gap that the alveolar tissue does not collapse under the effect of the pressure in the pleural gap.

On the other hand, too high of a value of the PEEP may have negative effects, especially during the inspiration phase. For, the lung tissue can be overextended at very high airway pressures during the inspiration phase. The necessary restriction of the maximum airway pressure at the end of the inspiration phase to values at which overextension of the lung tissue does not yet occur moreover results, at a high PEEP, in a restriction for the possible tidal pressure, i.e., the pressure difference between the pressure at expiration and the maximum pressure at inspiration.

Moreover, numerous studies also point out that a high value of the PEEP may impede the return flow of venous blood to the heart, with corresponding negative effects on the cardiovascular system.

In clinical practice, pressures such as PEEP or maximum possible tidal pressure and maximum airway pressure, respectively, are set by physicians or nursing staff of intensive care units on the basis of given physiological parameters of a patient or on the basis of known therapeutic benchmarks such as the so-called "ARDSnet Guidelines", see e.g., The Acute Respiratory Distress Syndrome Network, The New England Journal of Medicine, 2000. 342: pp. 1301-1308 or Grasso et al., American Journal of Respiratory Critical Care, 2007, 176: pp. 761-767. Such a setting usually is made in advance and is only sporadically readjusted by physicians or nurses.

Predetermined guidelines naturally are not suited to reflect the actual state of a patient, but merely give experience values. However, endeavors are being made to carry out the adjustment of pressures determinative for respiration, such as PEEP or maximum airway pressure, for each patient individually on the basis of the current state of the patient.

Known methods of deriving information concerning closed or overextended alveoli take considerable time during which patient respiration is not possible in a regular breathing cycle. This is the situation e.g., with static pressure/volume curves (PN curves) recorded with the aid of the "super syringe method", as described e.g., by Brochard L., Critical Care, 2006, 10: pp. 156-158. Moreover, during respiration there are occurring quite often inhomogeneous lung conditions in which closing of alveoli is to be observed in individual regions of the lung, but not in other regions. It is even possible that, with unchanged respiration parameters over a breathing cycle, the alveoli close during the expiration phase in some regions of the lung, whereas the alveoli are overextended during the inspiration phase in other regions of the lung. The known methods are not suited to resolve such conditions.

The method of electrical impedance tomography (EIT) described e.g., in Bikker et al., Critical Care, 2010, 14(3), R100; Tanaka, H. et al., American Journal of Respiratory and Critical Care, 2004, 169(7), pp. 791 to 800, or U.S. Pat. No. 6,502,984 B1 basically makes available a method allowing to gain real time information on the condition of the lung, in particular on the opening and closing of alveoli or overextension of alveoli. EIT is a non-invasive method that can be carried out directly at the patient's bedside and provides spatially differentiated information with regard to different regions of the lung. It is possible by means of EIT to differentiate regions of the lung with pathological conditions from regions "operating normally".

For example, EP 1 593 341 B1 suggests an EIT-based method of regionally determining the alveolar opening and alveolar closing of the lung. The effect to be exploited in this regard consists in that the change of an impedance signal gained by EIT, which is affected by the patient's respiratory movements, is larger in regions in which the lung has not yet collapsed than in regions with collapsed alveoli. For determining the change of the EIT impedance signal caused by respiratory movement, the distance between minimum and maximum values in the EIT impedance signal can be used for example.

Due to its large potential for obtaining information resolved in time and space with respect to the lung condition, there have been made numerous efforts to make EIT usable as a diagnosis instrument for assessing the course of lung diseases. There is also the wish to be able to use such information in mechanical respiration.

US 2010/0228143 A1 describes an apparatus and a method for determining functional lung characteristics of a patient on the basis of EIT signals. The EIT signals reflect a spatial distribution of the electrical impedance in a cross-section through the thorax of the patient. The impedance signals for the various EIT pixels distributed across the cross-sectional plane of the thorax are used for determining a global electrical impedance integrated over the entire cross-section. By way of the course of time of the global electrical impedance, a breathing cycle is identified and divided into various phases in time. In addition, the thoracic cross-sectional plane is divided into several regions, and in each phase of the breathing cycle and for each region, there is determined the ratio of the electrical impedance of the sub-region to the respective global electrical impedance. By way of the thus obtained time curves of the impedance ratio for the individual regions, it is possible to determine the intratidal gas distribution across the lung, i.e., the contribution of individual regions of the lung to respiration in the course of a respiration cycle. It is suggested to use this information also for determining various respiration parameters, such as e.g., the PEEP or the tidal volume.

Despite all investigations and efforts with respect to making EIT usable for the diagnosis of the lung condition, however, there have been no systems become available to the present day for controlling or regulating the pressures to be applied in mechanical respiration, which are capable of controlling the mechanical respiration by means of EIT signals in the sense of a closed-loop control largely without human intervention.

BRIEF SUMMARY

One or more embodiments of the underlying the present invention are directed to a system that provides for the possibility of a completely or at least largely automated patient-related adjustment or readjustment of a predetermined pressure set by the respiration device. The pressure set by the respiration device, for example, may be the positive end-expiratory pressure. Additionally or alternatively, it should be possible to adjust or readjust the maximum airway pressure or another pressure set by the respiration device on a completely or at least largely automated patient-related basis. In particular, the adjustment or readjustment of the pressure set by the respiration device is to be rendered possible with as little intervention as possible in the breathing cycle or respiration cycle (both terms will be used synonymously in the following) and possibly should necessitate no or just minor interventions by physicians or nurses.

One or more embodiments suggests a system for automated adjustment of a pressure set or specified by a respiration device, comprising an arrangement for electrical impedance tomography (EIT) for detecting an electrical impedance distribution along at least a two-dimensional cross-section through the human thorax at least at the end of an inspiration phase and at the end of an associated expiration phase; a device for dividing the detected electrical impedance distribution at the end of the inspiration phase and at the end of the expiration phase into a plurality of EIT pixels and for determining a value of the electrical impedance at the end of the inspiration phase and at the end of the expiration phase, as associated with a respective EIT pixel; and a device for automated adjustment of the pressure set by the respiration device on the basis of a comparison (i) of a deviation between the value of the electrical impedance at the end of the inspiration phase associated with an individual EIT pixel and the value of the electrical impedance at the end of the expiration phase associated with the respective individual EIT pixel (ii) with a deviation between the value of the electrical impedance at the end of the inspiration phase and the value of the electrical impedance at the end of the expiration phase, as determined on the basis of the entirety of the EIT pixels.

The basis of the automated determination of pressures set by the respiration device, such as e.g., the maximum airway pressure (in the following also briefly referred to as Paw_max) and/or the positive end-expiratory pressure (in the following also briefly referred to as PEEP) is the result of a distribution of the electrical impedance across an at least two-dimensional cross-section through the thorax of a patient obtained by electrical impedance tomography (in the following also briefly referred to as EIT). Such data can be obtained by means of known EIT arrangements in non-invasive manner and real time at the patient's bedside. The EIT data as a rule are determined on the basis of measurements of the electrical potential at a plurality of electrodes arranged in circumferentially distributed manner around the thorax, in reaction to application of a potential difference between two adjacent electrodes each, by back projection algorithms. With modern EIT apparatus the calculation of the impedance distribution is effected in automated manner by way of numeric algorithms. The impedance distribution then is present in the form of numerically calculated EIT values each associated with one of a plurality of EIT pixels arranged in the thoracic cross-sectional plane. The EIT pixels form a regular or irregular grid covering the thoracic cross-sectional plane. When the EIT data are present in a different form, e.g., as an analogous distribution of the impedance across the thoracic cross-sectional plane, corresponding rastering can be carried out. The EIT pixel distribution obtained from such rastering can be utilized directly as input quantity for automatic determination of the respiration pressure or pressures.

It is also conceivable to perform the rastering in accordance with a distribution of specific zones in the thoracic cross-sectional plane, for example to differentiate regions associated with specific organs from other regions or to make just a coarse distinction between rather dorsal and rather ventral regions when the patient is in a supine position.

In the following, for simplicity, there is assumed a grid of EIT pixels across a two-dimensional thoracic cross-section. It is to be noted that the ideas described for evaluating the EIT data are also applicable to EIT apparatus in which several cross-sectional planes of the thorax can be scanned in parallel, thus producing three-dimensional EIT images, as described e.g., in U.S. Pat. No. 6,501,198 B1.

One embodiment follows the basic idea of evaluating the impedance data delivered by EIT pixel for pixel. To this end, the impedance values associated with an individual EIT pixel are each compared with each other at the end of inspiration and at the end of the associated expiration, and the deviation thus arising is compared once more with a deviation between the impedance at the end of inspiration and the impedance at the end of the associated expiration, which is representative for the entirety of the pixels. The comparison is such that, by way of the comparison result thus gained, it is possible to derive an advisable exertion of influence on a pressure to be set in mechanical respiration, in particular the maximum airway pressure Paw_max and/or the positive end-expiratory pressure PEEP. Proceeding in this manner thus permits an automated adjustment or tracking of the desired respiration pressure by the respirator largely without human intervention.

For example, the afore-mentioned deviation between impedance values associated each with individual EIT pixels at the end of the inspiration and at the end of the associated expiration and/or the afore-mentioned difference between the impedance at the end of inspiration and the impedance at the end of the associated expiration, which is representative for the entirety of the pixels, can be defined in the form of a difference between the respective impedance values at the end of inspiration and at the end of expiration. As an alternative, it is also conceivable to define the deviation addressed as a ratio between the respective impedance values at the end of inspiration and at the end of expiration. Formation of a difference and formation of a ratio can also be combined, if desired. It is also conceivable to make use of still other parameters as long as these constitute a measure for the relative alteration of the respective impedance value between the end of inspiration and the end of expiration.

The afore-mentioned comparison can be in the form of a "yes/no" test. This means that an investigation is made by way of the comparison as to whether a predetermined condition is fulfilled, or whether this condition is not fulfilled. In this manner, the comparison delivers a simple criterion for deciding whether influence is to be taken by the respirator on the desired respiration pressure, i.e., whether the respective set pressure has to be increased or decreased, or whether this pressure can be maintained in unchanged form.

The respective end of an inspiration phase and the associated end of an expiration phase, respectively, can be determined by way of a single breathing cycle. However, it is also possible to use an impedance pattern over a breathing cycle as basis which results from the several breathing cycles by suitable averaging and/or integration.

In accordance with an embodiment, the deviation between the value of the electrical impedance at the end of the inspiration phase and the value of the electrical impedance at the end of the expiration phase, as determined on the basis of the entirety of the EIT pixels, can be a maximum value of all differences between the values of the electrical impedance at the end of the inspiration phase for respective ones of the EIT pixels and the values of the electrical impedance at the end of the expiration phase for said respective ones of the EIT pixel. The comparison then provides information as to whether the impedance change during a breathing cycle associated with a respective EIT pixel, as compared to the maximum impedance change in the thoracic cross-sectional plane during this breathing cycle, is rather small, rather large or rather average. By way of such data, it is quite easily and safely possible to derive from experience values or expert systems in how far influence is to be taken on the respiration pressure.

In additional embodiments, there may be provided in addition that the device for automated adjustment of the pressure set by the respiration device compares the deviation between the value of the electrical impedance at the end of the inspiration phase and the value of the electrical impedance at the end of the expiration phase, as associated with a respective EIT pixel, also with the value of the electrical impedance at the end of the inspiration phase and/or at the end of the expiration phase, as determined on the basis of the entirety of all EIT pixels each. Such a comparison with the value of the electrical impedance at the end of the inspiration phase provides information to the effect whether the impedance change during a breathing cycle, associated with a respective EIT pixel, belongs to a pixel in the thoracic cross-sectional plane at which the maximum airway pressure is rather small, rather large or rather average. Accordingly, a comparison with the value of the electrical impedance at the end of the expiration phase provides information as to whether the impedance change during a breathing cycle, associated with a respective EIT pixel, belongs to a pixel in the thoracic cross-sectional plane at which the airway pressure remaining at the end of the expiration phase is rather small, rather large or rather average. It is thus possible to make a distinction quite unequivocally as to whether an exertion of influence on the respiration pressure, which is advisable due to the impedance change between the impedance at the end of the inspiration phase and the impedance at the end of the expiration phase, is to be applied rather to the maximum airway pressure and/or the positive end-expiratory pressure.

In specific embodiments, the afore-mentioned comparison by pixels can be implemented such that the device for automated adjustment of the pressure set by the respiration device, by way of the comparison, determines those EIT pixels that fulfill a predetermined condition, and implements a correction of the set pressure when the percentage of EIT pixels fulfilling the condition is greater than a predetermined threshold value. This determines in essence the percentage of EIT pixels in the total number of EIT pixels in the thoracic cross-sectional plane that permits a conclusion of a physiologically undesired state. It is conceivable in this regard to select different sizes for the individual EIT pixels or to weigh the same differently in calculating the percentage. The condition can be determined on the basis of physiological findings. When the condition is fulfilled, this indicates a physiologically undesired state, e.g., collapsing of alveoli during the expiration phase, or overextension of alveoli during the inspiration phase.

In the event that the positive end-expiratory pressure (PEEP) set by the respiration device is to be automatically adjusted or readjusted, it is possible for example on the basis of a comparison (i) of a deviation between the value of the electrical impedance at the end of the inspiration phase associated with an individual EIT pixel and the value of the electrical impedance at the end of the expiration phase associated with the respective individual EIT pixel on the one hand, (ii) with a deviation between the value of the electrical impedance at the end of the inspiration phase and the value of the electrical impedance at the end of the expiration phase, as determined on the basis of the entirety of the EIT pixels, and the value of the electrical impedance at the end of the expiration phase, as determined on the basis of the entirety of the EIT pixels, on the other hand, to determine the percentage of EIT pixels in the thoracic cross-sectional plane which contain collapsed alveoli in a higher than negligible amount. If this percentage is above a predetermined first threshold value, it can be assumed that the PEEP is adjusted too low, and that the gas exchange in the lungs can be improved by increasing the PEEP.

For example, the value of the electrical impedance at the end of the expiration phase, as determined on the basis of the entirety of the EIT pixels, can be a minimum value of all values of the electrical impedance at the end of the expiration phase for respective ones of the EIT pixels. Thus, one takes the EIT pixel with the lowest impedance as reference quantity and determines from all EIT pixels a sub-quantity of EIT pixels having the lowest impedance. This sub-quantity of EIT pixels contains in essence all possible candidates for EIT pixels with collapsed alveoli. By way of the pixel-for-pixel comparison of the change in impedance over a breathing cycle of a respective EIT pixel with respect to the change in impedance determined on the basis of all EIT pixels, which comparison is provided for the sub-quantity in addition, it is possible to conclude relatively accurately those EIT pixels that contain collapsed alveoli.

As a result of comparisons of the type described, the device for automated adjustment of a positive end-expiratory pressure set by the respiration device is capable of associating those EIT pixels for which the comparison is positive with lung regions having collapsed alveoli. The term "positive" in this context is to mean that the respective EIT pixels fulfill a predetermined condition that is deemed characteristic of collapsed alveoli.

In specific embodiments, the association of EIT pixels with lung regions with collapsed alveoli can be implemented when the following two conditions are fulfilled:

$$EIT\_ei\_xy - EIT\_ee\_xy < k1 * \max(EIT\_ei\_xy - EIT\_ee\_xy; \text{for all possible xy})$$
AND
$$EIT\_ee\_xy < k2 * \min(EIT\_ee\_xy; \text{for all possible xy})$$

wherein:
- $EIT\_ei\_xy$: electrical impedance value at the end of the inspiration phase associated with a respective EIT pixel
- $EIT\_ee\_xy$: electrical impedance value at the end of the expiration phase associated with a respective EIT pixel,
- $0 \leq k1 \leq 1$, in particular $0.3 \leq k1 \leq 0.7$, in particular $0.4 \leq k1 \leq 0.6$, in particular $k1 = 0.5$;
- $k2 \geq 1$, in particular $1.0 \leq k2 \leq 1.6$, in particular $1.2 \leq k2 \leq 1.4$, in particular $k2 = 1.3$.

An elegant automatic adjustment or tracking of the positive end-expiratory pressure is achieved when the respiration device, in the event that the percentage of EIT pixels for which the comparison is positive exceeds a predetermined first threshold in the total number of EIT pixels, increases the value of the positive end-expiratory pressure for the subsequent breathing cycles by a predetermined amount. The second threshold value may be between 5 and 25%, and in particular may be 10%. For setting a value for the PEEP for the first time, a relatively low PEEP value (e.g., 10 cm $H_2O$) is used first and the respiration device is caused to increase the PEEP step by step (e.g., by 1 cm $H_2O$ per step) until the percentage of collapsed alveoli during expiration drops below the first threshold value. Thereafter, the PEEP is kept stable, until it is detected again that the percentage of collapsed alveoli during expiration reaches or exceeds the first threshold value. In reaction to this, the PEEP is again chosen higher in stepwise manner, until the value again drops below the first threshold value. The comparison can be repeated in predetermined intervals in time during respiration of the patient, and the positive end-expiratory pressure for the subsequent breathing cycles can be increased as long as the percentage of EIT pixels for which the comparison is positive in the total number of EIT pixels is below the first threshold value. With this automatic adjustment or readjustment of the PEEP which starts from a low PEEP level, there will generally also be determined an upper limit for the PEEP, in participate such that there is no barotrauma caused during respiration. It may be sufficient in this respect to manually set an upper limit for the PEEP that is deemed safe, e.g., such that the PEEP at all times is to remain lower than 25 cm $H_2O$.

Moreover, it may be provided that the value of the first threshold value is chosen higher with increasing value of the PEEP. This has the effect that with increasing levels of the PEEP, a further increase takes place only when increasingly higher percentage of the EIT pixels has collapsed alveoli. It can thus be ensured that the value of the PEEP is not increased eternally when the percentage of EIT pixels with collapsed alveoli does not decrease or decreases only slightly with increasing PEEP. For example, with each increase of the PEEP, the first threshold value may be increased by an amount between 0.3 and 3%, in particular by 1%.

In the event that, in addition to or as an alternative to the positive end-expiratory pressure, the maximum airway pressure Paw_max set by the respiration device is to be adjusted or readjusted automatically, it is possible for example on the basis of a comparison (i) of a deviation between the value of the electrical impedance at the end of the inspiration phase associated with an individual EIT pixel and the value of the electrical impedance at the end of the expiration phase associated with the respective individual EIT pixel, on the one hand, (ii) with a deviation between the value of the electrical impedance at the end of the inspiration phase and the value of the electrical impedance at the end of the expiration phase, as determined on the basis of the entirety of the EIT pixels, as well as the value of the electrical impedance at the end of the inspiration phase, as determined on the basis of the entirety of the EIT pixels, on the other hand, to determine the percentage of EIT pixels in the thoracic cross-sectional plane having overextended alveoli in a higher than negligible amount. In case this percentage is above a predetermined second percentage threshold that is independent of the first percentage threshold for setting the PEEP, it may be assumed that the maximum airway pressure is adjusted too high, and that the lung tissue can be strained less or protected by reducing the maximum airway pressure. The reduction of the maximum airway pressure—with unchanged PEEP—can be achieved via a reduction of the maximum tidal pressure. If it is advisable to select a lower value for the PEEP in the subsequent breathing cycles, the reduction of the PEEP can be considered in reducing the maximum airway pressure, so that the influence on the maximum tidal pressure is compensated at least in part.

For example, the value of the electrical impedance at the end of the inspiration phase, as determined on the basis of the entirety of the EIT pixels, can be a maximum value of all values of the electrical impedance at the end of the inspiration phase for a respective one of the EIT pixels. This means, that the EIT pixel in the thoracic cross-sectional plane with the highest impedance is used as reference quantity for determining from all EIT pixel an additional sub-quantity of EIT pixels having the highest impedance at the end of the inspiration phase. Possible EIT pixels with overextended alveoli should be contained in this additional sub-quantity so that a search for those pixels in which overextension of alveoli has actually occurred is to be carried out within this sub-quantity only. If the suggested pixel-for-pixel comparison of the change in impedance between the end of inspiration and the end of expiration is carried out for all EIT pixels of this sub-quantity, it is possible to identify relatively exactly those EIT pixels that have overextended alveoli.

In similar manner as described hereinbefore, the device for automated adjustment of a maximum airway pressure set by the respiration device can associate those EIT pixels for which the comparison is positive with lung regions having overextended alveoli. "Positive comparison" again means that the respective EIT pixels fulfill a predetermined condition that is deemed to be characteristic of an overextension of alveoli.

In embodiments, the association of EIT pixels with lung regions having overextended alveoli can take place when the following two conditions are fulfilled:

EIT_ei_xy − EIT_ee_xy < k3 * max(EIT_ei_xy − EIT_ee_xy;
for all possible xy)
AND
EIT_ei_xy > k4 * max(EIT_ei_xy; for all possible xy)
wherein:
- EIT_ei_xy: electrical impedance value at the end of the inspiration phase associated with a respective EIT pixel
- EIT_ee_xy: electrical impedance value at the end of the expiration phase associated with a respective EIT pixel,
- 0 ≤ k3 ≤ 1, in particular 0.3 ≤ k3 ≤ 0.7, in particular 0.4 ≤ k3 ≤ 0.6, in particular k3 = 0.5;
- 0 ≤ k4 ≤ 1, in particular 0.5 ≤ k4 ≤ 0.9, in particular 0.6 ≤ k4 ≤ 0.8, in particular k4 = 0.7.

An elegant automatic adjustment or readjustment can also be achieved for the maximum airway pressure when the device for automatic adjustment of a maximum airway pressure set by the respiration device decreases the value of the maximum airway pressure for the subsequent breathing cycles by a predetermined amount, when the percentage of EIT pixels for which the comparison is positive in the total number of EIT pixels exceeds a predetermined second threshold value. The second threshold value may be in the range between 5 and 25%, and in particular may be 10%. For setting a value for the maximum airway pressure for the first time, a relatively high value for the maximum airway pressure (e.g., 40 cm H$_2$O) is used first and the respiration device is caused to decrease the maximum airway pressure step by step (e.g., by 1 cm H$_2$O per step) until the percentage of overextended alveoli during inspiration drops below the second threshold value. Thereafter, the maximum airway pressure is kept stable, until it is detected again that the percentage of extended alveoli during inspiration again reaches or exceeds the second threshold value. In reaction to this, the maximum airway pressure is again reduced in stepwise manner, until the value again drops below the second threshold value. The comparison can be repeated in predetermined intervals in time during respiration of the patient, and the maximum airway pressure for the subsequent breathing cycles can be reduced until the percentage of EIT pixels for which the comparison is positive in the total number of EIT pixels is below the second threshold value. The initial value for the maximum airway pressure can be set manually. In general, a value will be selected which, though being above the value to be set in optimum manner, is still sufficiently low so that respiration over a small number of breathing cycles does not yet cause serious damage to the lung tissue of the patient.

A usual value for the initial maximum airway pressure is for example 40 cm H$_2$O.

Moreover, also in setting the maximum airway pressure it may be provided that the value of the second threshold value is chosen higher with a decreasing value of the maximum airway pressure. This measure makes sure that the respiration device does not reduce the maximum airway pressure down to zero when, in an exceptional case, the percentage of EIT pixels with overextended alveoli is not reduced or only insignificantly reduced with a decreasing maximum airway pressure. Rather, the increase in the second threshold value with a decreasing maximum airway pressure will be selected such that a maximum airway pressure moderately above the PEEP is obtained at all times. For example, with each decrease of the maximum respiration pressure, the second threshold value can be increased by an amount between 0.3 and 3%, in particular by 1%.

In further embodiments, the arrangement for electrical impedance tomography (EIT) can detect an electrical impedance distribution in the form of electrical impedance values associated with EIT pixels arranged in a predetermined grid. In the event that the EIT arrangement already yields a suitably rasterized image of impedance values, the device for dividing the detected electrical impedance distribution into a plurality of EIT pixels can associate exactly the respective value of the electrical impedance with a respective grid element. As an alternative, the rastering delivered by the EIT in the form of EIT elementary pixels can also be converted by calculation into another desired rastering in the form of EIT pixels illustrating an image of the thoracic cross-sectional plane, and a corresponding impedance value can be associated with each of the EIT pixels.

The EIT signals detected by the EIT arrangement often have higher-frequency signal components superimposed thereon that have nothing to do with the breathing cycle or the respiration cycle, respectively. An example are cardiac factors since also the activity of the cardiovascular system takes influence on the impedance in some regions of the thoracic cross-sectional plane. Due to the fact that cardiac factors are subject to a significantly higher clock frequency, such interference effects can be filtered out by a filter device.

The filter device, for example, is a low-pass filter or a band-pass filter with suitable cut-off frequency that is connected in the signal path of the EIT signals. A respiration device with corresponding low-pass function for filtering out cardiac effects is known for example from DE 103 01 202 B3.

At least one embodiment also relates to a device for mechanical respiration, comprising a system for automatic adjustment of a pressure set by the respiration device having at least one of the features described hereinbefore. The respiration device can be designed for permanent respiration of patients, e.g., in intensive care units, and in particular can implement the adjustment of the pressures mentioned in largely automatic manner, with only sporadic intervention by physicians or nursing staff.

According to a further aspect, one embodiment of the present invention relates to a method for automated adjustment of a pressure set by a respiration device, in particular a positive end-expiratory pressure (PEEP) and a maximum airway pressure (Paw_max), wherein with the aid of an arrangement for electrical impedance tomography (EIT) an electrical impedance distribution is detected along at least a two-dimensional cross-section through the human thorax at least at the end of an inspiration phase and at the end of an associated expiration phase, the detected electrical impedance distribution at the end of the inspiration phase and at the end of the expiration phase is divided into a plurality of EIT pixels and a respective value of the electrical impedance at the end of the inspiration phase and at the end of the expiration phase is associated with each one of the EIT pixels, and the pressure set by the respiration device is determined on the basis of a comparison (i) of a deviation between the value of the electrical impedance at the end of the inspiration phase associated with an individual EIT pixel and the value of the electrical impedance at the end of the expiration phase associated with the respective individual EIT pixel (ii) with a deviation between the value of the electrical impedance at the end of the inspiration phase and the value of the electrical impedance at the end of the expiration phase, as determined on the basis of the entirety of the EIT pixels. Such a method can be developed further in particular in accordance with one or several of the afore-mentioned further development features.

BRIEF DESCRIPTION OF THE SEVERAL VIEWS OF THE DRAWINGS

The invention will be explained in detail in the following by way of embodiments shown in the drawings in which:

FIGS. 3a to 3e show illustrations corresponding to FIGS. 2a to 2e, however for lungs with collapsed alveoli during the expiration phase.

DETAILED DESCRIPTION

Figure 1:
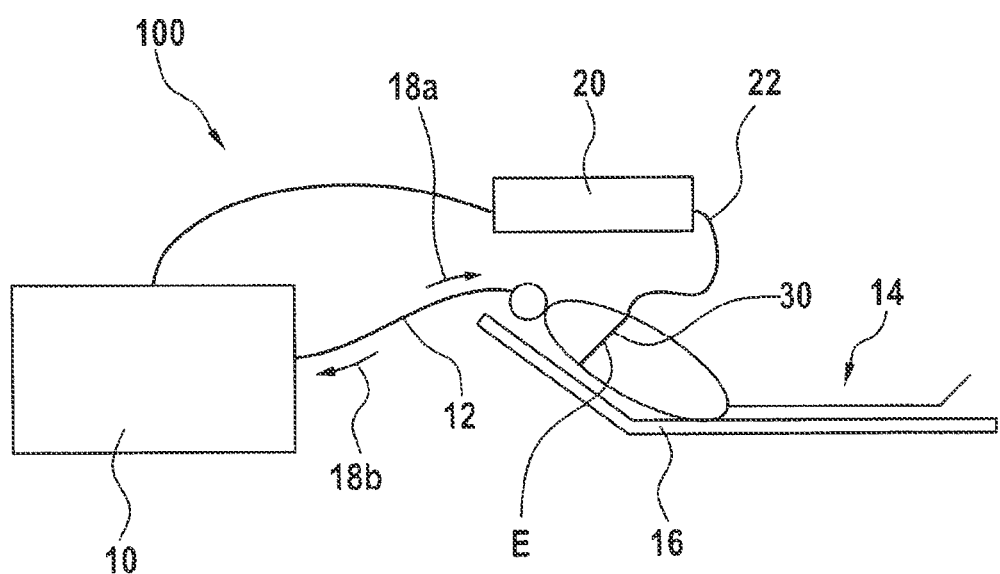
FIG. 1 shows a highly simplified and schematic illustration of the essential elements of a respiration device with EIT arrangement for detecting electrical impedance signals along a thoracic cross-section.

FIG. 1 shows, in a highly schematic representation and in the form of a block diagram, the essential elements of a respiration device 100 comprising a respirator 10 for generating breathing gas flows and breathing pressures, respectively, and for controlling breathing, as well as an electrical impedance (EIT) arrangement 20. The EIT arrangement serves to detect values of the electrical impedance in the tissue of a patient, outlined schematically at 14, along a cross-section through the thorax of the respirated patient 14, indicated with the letter E in FIG. 1 and extending from the dorsal to the ventral side in the present example. From the detected data, the EIT arrangement 20 calculates images reflecting the course of the electrical impedance across the thoracic cross-section E.

The respiration device 100 is shown in FIG. 1 in a state with intubated windpipe (trachea) of the respirated patient, using a respiration hose 12. The patient 14 is lying in a supine position in a hospital bed 16, as a rule in an intensive care unit. The tube of the respiration device 100 is pushed a certain distance into the trachea, usually via the mouth opening (not shown) of the patient, in order to supply respiration gas to the airway during an inspiration phase of the breathing cycle. During an expiration phase following the inspiration phase, exhaled air is discharged via the tube 14 as well, which branches at its end connected to the ventilator 10 into a first end and a second end. The first end of the tube is connected via an airway inlet valve to an airway inlet connector of the respirator 10 for applying respiration gas under an inspiration pressure PInsp. The second end of the tube is connected via an airway outlet valve to an airway outlet connector of the respirator 10 for application of an expiration pressure PExp. The airway inlet valve and the airway outlet valve, during the cyclically repetitive breathing cycle, are opened in alternating manner in order to apply the inspiration pressure PInsp or the expiration pressure PExp to the respiration hose 12.

Both the inspiration pressure PInsp and the expiration pressure PExp are generated by the respirator 10 according to predetermined time patterns, in order to generate periodically repetitive breathing cycles. In each breathing cycle, respiration gas to be inhaled during the inspiration phase flows towards the lungs of the patient 14, as illustrated in FIG. 1 by arrow 18a. During the subsequent expiration phase, the breathing gas to be exhaled flows back from the lungs of the patient to the respirator 10, as indicated by arrow 18b. During the inspiration phase, the airway inlet valve normally remains open, and the inspiration pressure PInsp—which as a rule is larger than the expiration pressure PExp—is applied to the airway entrance. During the expiration phase, the airway inlet valve 18 is closed and the airway outlet valve is open. In this situation, the expiration pressure PExp is applied to the airway entrance.

In connection with the present invention, any forms of known respiration patterns can be used, for example, pressure-controlled respiration modes, volume-controlled respiration modes or also respiration modes combining pressure-controlled and volume-controlled aspects. In addition to purely machine-controlled respiration modes, in which the time course of the inspiration pressure PInsp and possibly also of the expiration pressure PExp are determined by the respirator 10, there are also respiration modes conceivable in which spontaneous breathing efforts of the patient can either support the machine respiration, or the machine respiration serves to support spontaneous breathing endeavors of the patient. With such types of respiration, the time course of inspiration pressure PInsp and expiration pressure PExp, respectively, and often also the position of the inlet valve 18 and outlet valve 24, respectively, are not determined solely by the respirator 10 but are influenced also by the spontaneous breathing endeavors of the patient.

The breathing gas may contain ambient air, but will usually contain a predetermined percentage of pure oxygen, which is often referred to as FiO2, which is higher than the oxygen content of the ambient air. Moreover, the breathing gas as a rule is also humidified.

The flow of breathing gas at the airway entrance is determined by means of an airway entrance flow sensor, not shown. The airway entrance flow sensor is based on detecting a pressure difference dP between an input volume and an output volume communicating with the input volume, and provides for a determination of the breathing gas mass flow at the airway entrance. It is quite easily possible to derive from the pressure signal in the output volume at the same time the value of the airway inlet pressure Paw. The airway inlet pressure Paw is the pressure applied to the lungs during inspiration. This pressure is somewhat higher than the breathing pressure actually prevailing in the lungs. During mechanical respiration, the breathing pressure in each breathing cycle, during the inspiration phase, is increased in ramp-like manner from a low starting value, until a high final value is reached at the end of the inspiration phase, which possibly is maintained for a certain period of time. In this phase of the breathing cycle, a maximum airway pressure Paw_max arises in the lungs. The maximum airway pressure Paw_max could generally be measured at the airway entrance at the end of the inspiration phase, provided that a complete pressure balance is created. The airway inlet pressure Paw measured at the end of the inspiration phase then would reflect the maximum airway pressure in quite good approximation. As the inspiration phase is followed by the expiration phase, such complete pressure balance often is not reached in practical application, unless at the end of the inspiration phase there is artificially performed a brief occlusion maneuver for approx. 1 to 5 s, i.e., airway entrance valve and airway exit valve remain closed at the same time. However, such maneuvers interrupt the breathing cycle and thus are not carried out on a regular basis during respiration.

During the expiration phase, there is no tidal pressure applied to the airway entrance, but rather the air present in the lungs is to be pushed out of the lungs as a consequence of relaxation movement of the lung tissue. However, also during the expiration phase, the respiration hose 12 and thus the airway entrance often has a positive pressure applied thereto. This pressure is referred to as positive end-expiratory pressure, or briefly PEEP, and is to prevent that alveoli in some portions of the lungs collapse during the expiration phase under the pressure from the thorax acting on weakened lung tissue. During respiration with PEEP, the tidal pressure finally driving the breathing gas flow presents itself as a difference between the respiration pressure and the PEEP.

The pressure prevailing in the alveoli of the lungs is dependent on the airway inlet pressure Paw and the flow of breathing gas into the lungs and out of the lungs, respectively. In the event of a pressure balance between airway entrance and alveoli, the alveolar pressure Palv is equal to the airway inlet pressure. The consequence of such a pressure balance is that the flow of breathing gas comes to a standstill. For example, a brief occlusion maneuver (having a length of approx. 1 to 5 s) can result in a pressure balance. When the gas flow in the airway comes to a halt, the alveolar pressure Palv can be determined by determining the airway inlet pressure Paw. With uninterrupted breathing cycles, there is indeed a minimum value of the pressure Paw measured at the airway entrance at the end of the expiration phase. However, this pressure normally is slightly above the set PEEP.

Both in case of physiological respiration as well as in case of mechanical respiration, the flow of breathing gas is determined by a pressure difference between the alveolar pressure Palv and airway inlet pressure Paw.

In case of purely physiological breathing, a negative pressure differential, i.e., a vacuum, between the alveolar pressure Palv and airway inlet pressure Paw is generated for inhaling, by expansion of the thorax and associated lowering of the pressure in the pleural gap formed between the thorax and the lungs. Exhalation takes place passively by relaxation of the thorax and elastic recovery of the lung tissue. For this reason, the pressure in the pleural gap in case of physiological respiration is always lower than the alveolar pressure.

With mechanical respiration, the breathing gas is pumped into the lungs with positive pressure—the positive tidal pressure. For this reason, the airway inlet pressure Paw=PInsp in case of mechanical respiration, during the inspiration phase, is greater than the alveolar pressure Palv, and the latter in turn is greater than the pressure in the pleural gap Ppl. During expiration, an airway pressure PExp is applied to the airway entrance which is lower than the alveolar pressure Palv so that breathing gas flows out from the alveoli. In case of a very small airway pressure PExp, it may happen that at the end of expiration, when only very little gas is still present in the lungs, the pressure in the pleural gap Ppl exceeds the alveolar pressure Palv to such an extent that part of the alveoli of the lungs collapses.

The collapse of the alveoli can be prevented when an additional positive pressure is applied to the airway entrance in the expiration phase as well. A positive airway pressure then is applied permanently, i.e., both during the inspiration phase and during the expiration phase, to the airway entrance. This positive airway pressure is referred to as positive end-expiratory pressure or PEEP.

In FIG. 1, numeral 20 designates an additional device for electrical impedance tomography (EIT). The EIT device 20 is connected, by way of a cable connection 22, to a breast belt 30 strapped around the thorax of the patient at breast level. The breast belt 30, along the length thereof, is provided with electrical electrodes (not illustrated) in regular intervals. The electrodes directly abut the skin around the thorax of the patient 14. The EIT device 20 thus is capable of conducting electrical current into the body of the patient 14 via the cable connection 22 and the electrodes arranged on the breast belt 30. The electrodes on the breast belt, in turn, can serve as sensors for detecting electrical current flowing through the body of the patient 14. The EIT device 20 is capable of individually controlling the electrodes in breast belt 30. The EIT device 20 thus is adapted to apply an electrical voltage between two respective arbitrary electrodes—which as a rule are adjacent ones for reasons of calculation—of the breast belt 30. In response to application of such voltages, there are electrical currents flowing in the thorax of the patient. Also via the remaining electrodes on the breast belt 30, the EIT device 20 can detect, all around the thorax, these electrical currents flowing in the thorax between two respective electrodes of the breast belt in response to application of the electrical voltage, and can derive therefrom corresponding values of the electrical impedance in spatially resolved manner. Thus, a distribution of the electrical impedance in the thoracic cross-sectional plane E defined by the breast belt 14 can be detected in real time and in the non-invasive manner.

By way of the impedance signal provided by means of EIT, or by way of the spatial distribution of the electrical impedance in the thoracic cross-sectional plane, it is possible to conclude the breathing gas present in the lungs. The distribution of the electrical impedance in the thoracic cross-sectional plane is a direct measure for breathing gas present in the lungs. Regions with a high gas content appear as values of high impedance in an EIT image, whereas regions with low gas content appear as regions of low impedance. By way of spatial and/or time changes of the electrical impedance signal delivered by EIT, it is basically possible to recognize the collapse of alveoli under pressure from outside during expiration as well as overextension of alveoli under pressure from the airway entrance during inspiration. Impedance images provided by EIT thus can be used as basis for adjusting specific gas pressures to be pre-set in mechanical respiration, in particular the PEEP and/or the maximum airway pressure. This can be implemented manually, by a physician or nursing staff performing an EIT measurement, observing the impedance pattern in the thoracic cross-sectional plane thus obtained and then adjusting the said pressures accordingly.

The present invention suggests to use the spatially and time resolved values of the electrical impedance obtained by EIT as basis for a largely automated adjustment, i.e., an adjustment which on principle is possible without human intervention, of pressures relevant for mechanical respiration, such as PEEP or maximum airway pressure Paw_max. This is achieved with the aid of a specific kind of evaluation of the impedance distributions obtained by EIT. This evaluation is based on a comparison of values of the electrical impedance associated with individual EIT pixels in the thoracic cross-section E with a value of the electrical impedance reflecting a characteristic property of the entirety of all EIT pixels in the thoracic cross-sectional plane. This comparison is evaluated, EIT pixel for EIT pixel, for all EIT pixels of the thoracic cross-sectional plane. By way of the relative occurrence of EIT pixels fulfilling one or several predetermined conditions, it is possible to derive criteria as to whether, for example, a set value for the PEEP is sufficiently high for preventing collapse of alveoli, and/or whether a set value for the maximum airway pressure Paw_max is sufficiently low for preventing overextension of alveoli. The principle behind this idea shall be explained in the following by way of FIGS. 2a to 2e, 3a to 3e and 4a to 4e.

Figure 2A:
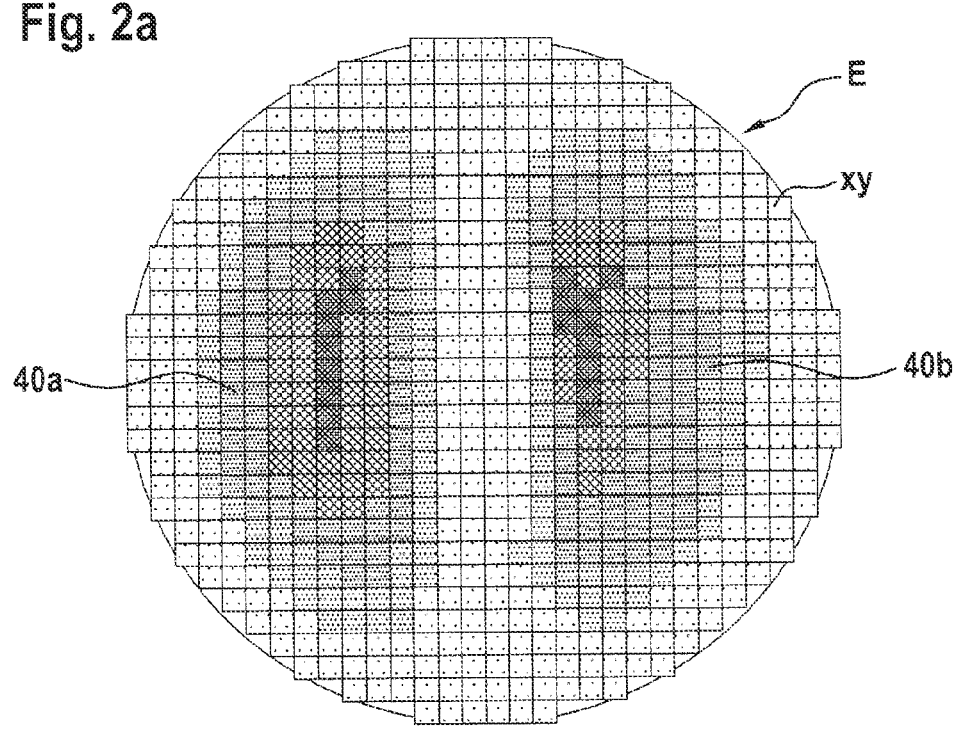
FIG. 2a shows a schematic illustration of electrical impedance values rasterized in the form of a regular grid of EIT pixels across the thoracic cross-section of FIG. 1 at the end of the inspiration phase in case of healthy lungs.
Figure 2B:
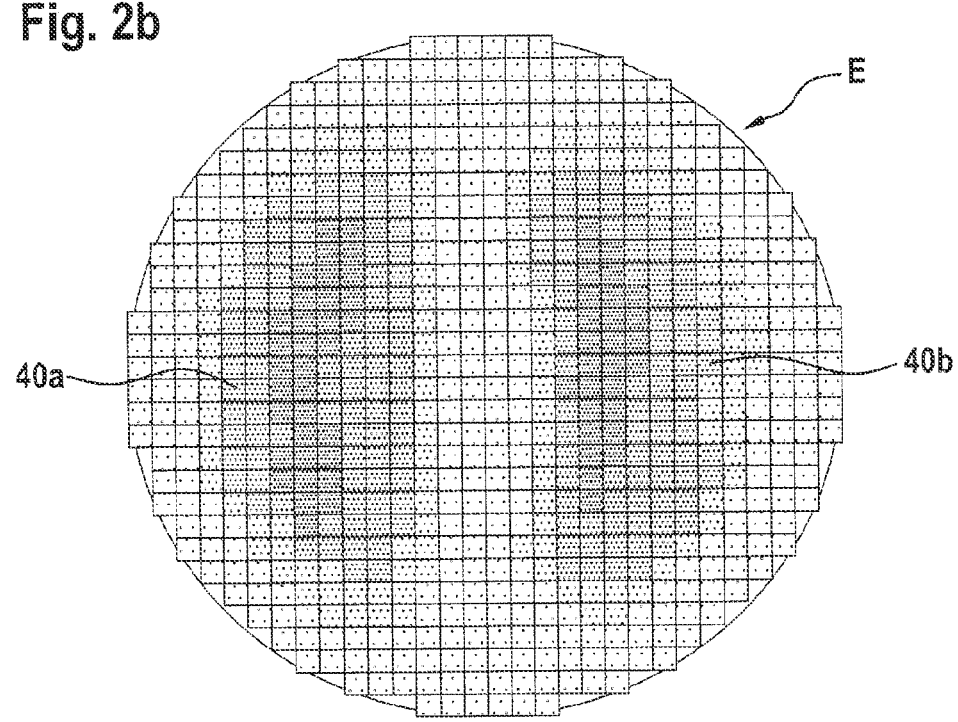
FIG. 2b shows a schematic illustration of electrical impedance values rasterized in the form of a regular grid of EIT pixels across the thoracic cross-section of FIG. 1 at the end of the associated expiration phase in case of healthy lungs.

FIGS. 2a to 2e, 3a to 3e and 4a to 4e illustrate the thoracic cross-sectional plane E in simplified manner in the form of a circle each. The thoracic cross-sectional plane E is divided into a grid-like pattern of individual EIT pixels which in total fill the entire cross-sectional plane E within the thorax. In FIGS. 2a and 2b, a respective one of the EIT pixels is referenced xy for illustration. It can be said that this EIT pixel is located in row x (in the example row 8 counted from above) and in column y (in the example column 28 counted from the left), so that all EIT pixels can be identified unequivocally by a pair of numerical values x (=row) and y (=column). It is to be noted that such an arrangement of EIT pixels xy can be provided directly by the EIT device 20. However, it is just as conceivable to calculate an arrangement of EIT pixels xy, as illustrated in FIGS. 2a to 2e, from an arbitrary impedance distribution delivered by the EIT device. In addition, a regular pattern of the EIT pixels, as shown in FIGS. 2a to 2e, is not cogently necessary. The individual EIT pixels xy can also be arranged in completely irregular manner and/or may have completely different sizes and/or completely different shapes. However, there should be largely no regions of the thoracic cross-sectional plane E taken by the patient's lungs that are associated with none of the EIT pixels.

FIGS. 2a and 2b schematically show for each EIT pixel xy impedance values at the end of the inspiration phase EIT_ei_xy (FIG. 2a) and impedance values at the end of the associated expiration phase EIT_ee_xy (FIG. 2b), for healthy lungs 40. In the two figures, the value of the electrical impedance is coded by gray values each, with dark locations corresponding to EIT pixels xy with high impedance EIT_ei_xy and EIT_ee_xy, respectively, and bright locations corresponding to EIT pixels xy with low impedance EIT_ei_xy and EIT_ee_xy, respectively. Values of high electrical impedance indicate regions with a high content of breathing gas, whereas values of low impedance indicate regions with a low content of breathing gas. FIGS. 2a and 2b clearly reveal the lungs 40 of the patient 14 with right lobe 40a of the lungs and left lobe 40b of the lungs.

Components of the EIT signals or impedance values that are due to other organs than the lungs 40 are omitted in FIGS. 2a and 2b (just as in all following FIGS. 2c to 2e, 3a to 3e, 4a to 4e). For example, EIT signal components due to cardiac effects can be filtered out from the originally obtained EIT signals by way of the frequency of the heart that is clearly higher in comparison with the respiration frequency, by application of corresponding low-pass or band-pass filters, as described for example in DE 103 01 202 B1.

In FIG. 2a—at the end of the inspiration phase—, the individual EIT pixels xy associated with the lungs 40 are shaded in general in darker color than the respectively associated EIT pixels xy in FIG. 2b—at the end of the expiration phase. This complies with the fact that, at the end of the inspiration phase, any region of the lungs should contain an in total higher percentage of breathing gas than at the end of the expiration phase, at least in healthy lungs.

Figure 2C:
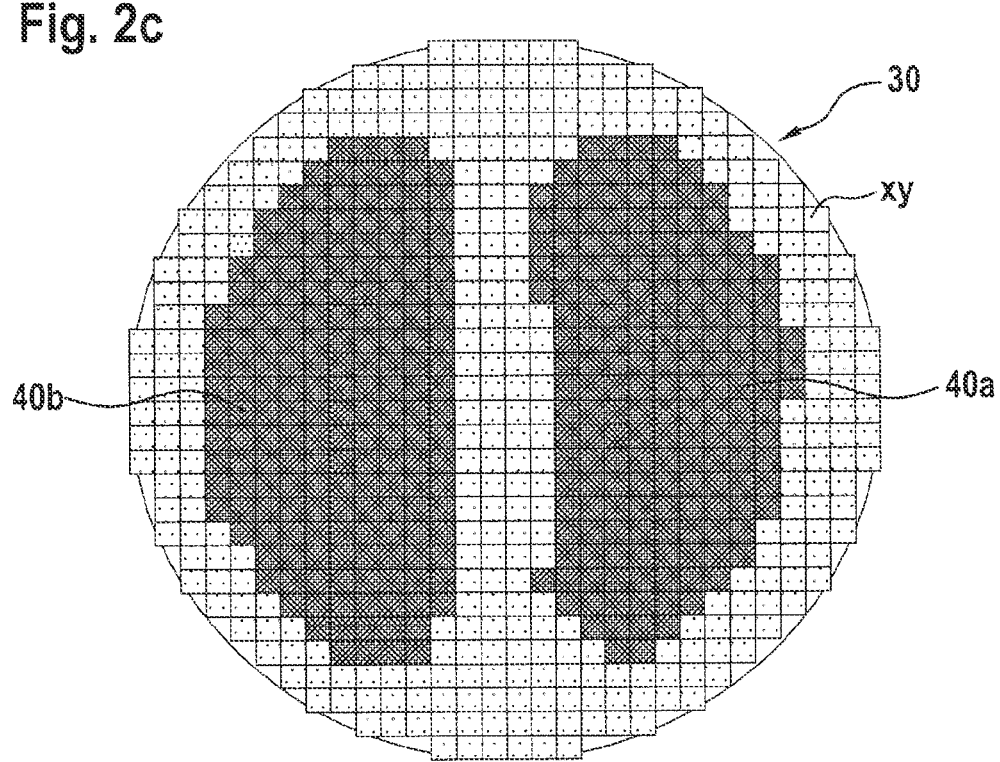
FIG. 2c shows a schematic illustration of the rasterized EIT pixels of FIGS. 2a and 2b, with pixels in which the impedance difference between the end of the inspiration phase and the end of the expiration phase is at least as large as 0.5 times the maximum impedance difference between the end of the inspiration phase and the end of the expiration phase among all EIT pixels in the thoracic cross-section being shown shaded in dark color and all EIT pixels with a corresponding impedance difference of less than 0.5 times the maximum impedance difference being shown shaded in light color.

This finding can be taken from FIG. 2c relatively clearly. This figure shows a further schematic illustration of the rasterized EIT pixels xy of FIGS. 2a and 2b. However, FIG. 2c shows for each EIT pixel xy in the thoracic cross-sectional plane E the impedance difference between the impedance EIT_ei_xy detected at the end of the inspiration phase and the impedance EIT_ee_xy detected at the end of the expiration phase. The representation of the impedance difference in FIG. 2c is "binarized" in the sense that all EIT pixels xy fulfilling a predetermined condition are shaded in dark color, and all other EIT pixels not fulfilling this condition are shaded in light color. In case of FIG. 2c, the predetermined condition is that all those EIT pixels xy are shaded in dark in which the afore-mentioned impedance difference is at least as large as 0.5 times the maximum impedance difference EIT_ei_xy−EIT_ee_xy between the impedance at the end of the inspiration phase EIT_ei_xy and the impedance at the end of the expiration phase EIT_ee_xy occurring among all EIT pixels xy in the thoracic cross-section E. This is expressed in a formula as follows:

EIT pixels xy are shaded in dark color when the following holds:
$$EIT\_ei\_xy - EIT\_ee\_xy \geq 0.5 * \max(EIT\_ei\_xy - EIT\_ee\_xy;$$
for all possible xy),
wherein
EIT_ei_xy: electrical impedance value at the end of the inspiration phase associated with a respective EIT pixel
EIT_ee_xy: electrical impedance value at the end of the expiration phase associated with a respective EIT pixel.

In contrast thereto, all other EIT pixels with a corresponding impedance difference of less than 0.5 times the maximum impedance difference are shaded in light color in FIG. 2c.

It can easily be seen that in virtually all regions of the lungs 40 the impedance difference is greater than the threshold value defined in this example. Due to the fact that the threshold value is determined to be half of the maximum impedance difference occurring in the thoracic cross-section E between the end of inspiration and the end of expiration, it follows from this finding that, for all EIT pixels xy, the impedance difference is scattered around just a small value in comparison with the maximum impedance difference.

This means that, with respect to all regions of the lungs, there is visible a clear difference as regards the filling of alveoli with breathing gas at the end of inspiration as compared to the remaining volume remaining in the alveoli at the end of expiration. This is a strong indication to the effect that all regions of the lungs work normally and that neither collapsed nor overextended alveoli are present.

Figure 2D:
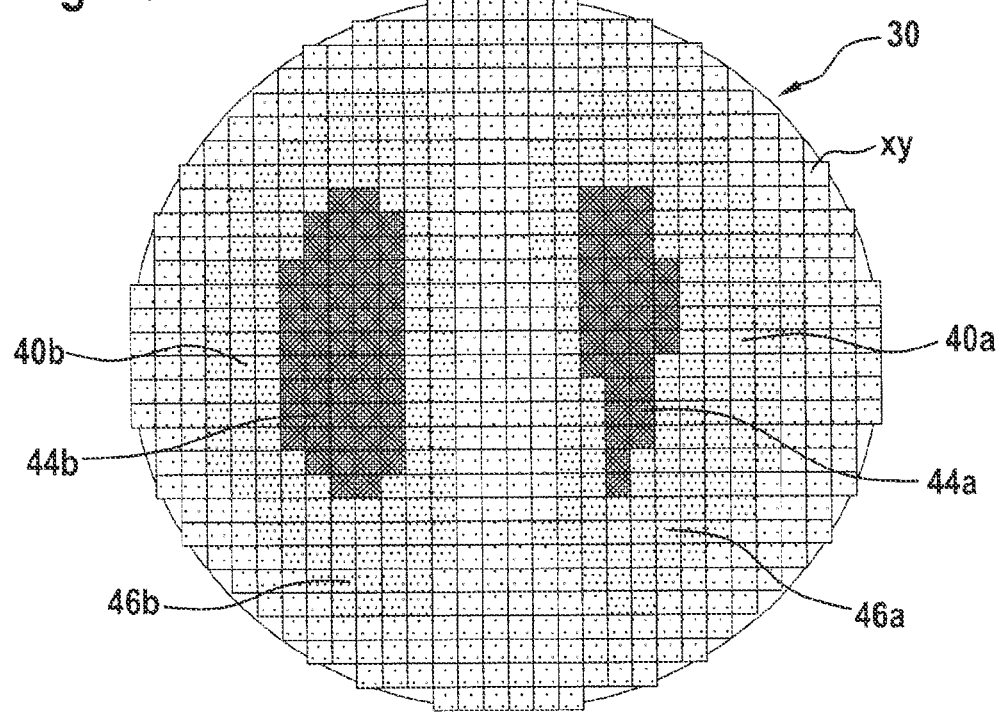
FIG. 2d shows a schematic illustration of the rasterized EIT pixels of FIGS. 2a and 2b, with EIT pixels having impedance values at the end of the inspiration phase that are greater than 0.7 times the maximum impedance at the end of the inspiration phase among all EIT pixels in the thoracic cross-section being shown shaded in dark color, and pixels having impedance values at least as high as 0.7 times the maximum impedance being shown shaded in light color.

FIG. 2d shows an illustration of the thoracic cross-sectional plane E with rasterized EIT pixels xy that is quite similar to FIG. 2c. FIG. 2c finally shows a binarized version of the impedance distribution at the end of the inspiration that is already shown in FIG. 2a. Shaded in dark in FIG. 2c are those EIT pixels xy of FIG. 2a that have impedance values at the end of the inspiration phase EIT_xy_ei associated therewith that are greater than 0.7 times the maximum impedance EIT_ei_max occurring among all EIT pixels xy in the thoracic cross-sectional plane E at the end of the inspiration phase. Shaded in light color are all remaining EIT pixels xy having impedance values at the end of the inspiration phase EIT_xy_ei associated therewith which at the most are 0.7 times the maximum impedance EIT_ei_max occurring among all EIT pixels xy in the thoracic cross-sectional plane E at the end of the inspiration phase. This is expressed in a formula as follows:

EIT pixels xy are shaded in dark color in FIG. 2d when the following holds:
$$EIT\_ei\_xy > 0.7 * EIT\_ei\_max,$$
EIT Pixel xy are shaded in light color in FIG. 2d when the following holds:
$$EIT\_ei\_xy \leq 0.7 * EIT\_ei\_max,$$
wherein: $EIT\_ei\_max = max(EIT\_ei\_xy;$ for all possible xy)

It is quite easily possible to perceive in FIG. 2d a respective central region 44a, 44b of the two lobes 40a, 40b of the lungs, in which there is a tendency for high breathing gas pressures prevailing at the end of inspiration, as well as a respective peripheral region 46a, 46b in which there is a tendency for low breathing gas pressures prevailing at the end of inspiration. As shown in FIG. 2c, the impedance difference between the end of inspiration and the end of expiration, however, is in all regions of the lungs 40 above the threshold value, which indicates that the alveoli in all regions of the lungs participate in normal manner in the exchange of gas, irrespective of whether a high or merely a moderate breathing gas pressure is prevailing at the end of inspiration.

Figure 2E:
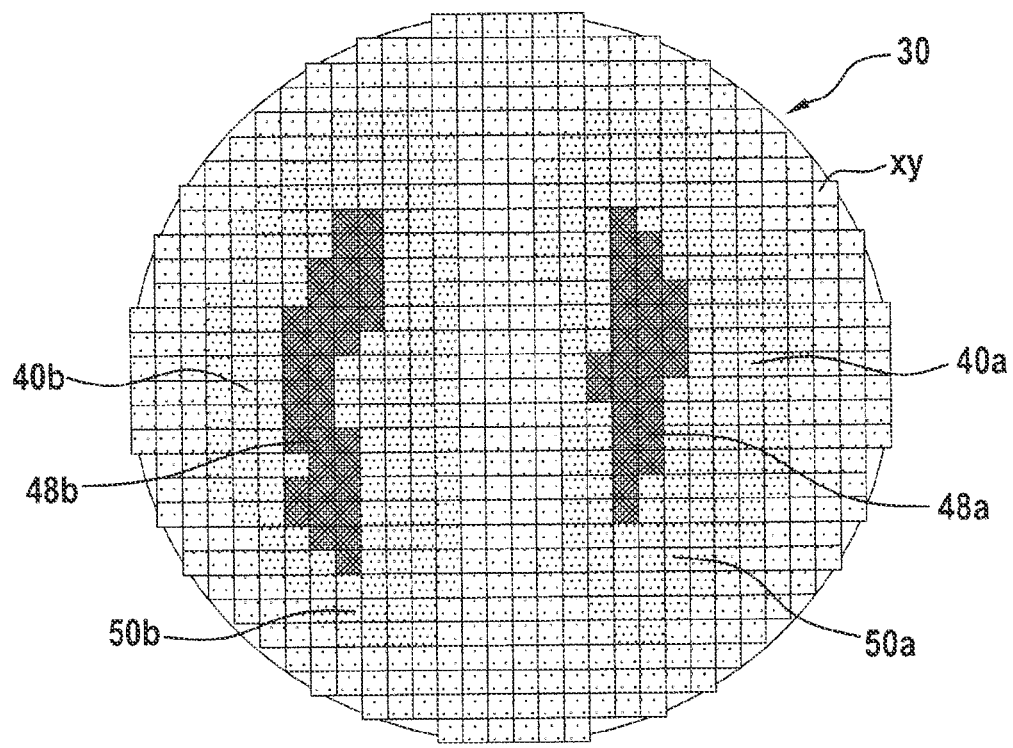
FIG. 2e shows a schematic illustration of the rasterized EIT pixels of FIGS. 2a and 2b, with EIT pixels having impedance values at the end of the expiration phase that are at least equal to 1.3 times the minimum impedance at the end of the expiration phase among all EIT pixels in the thoracic cross-section being shown shaded in dark color, and pixels having impedance values less than 1.3 times the minimum impedance being shown shaded in light color.

FIG. 2e shows another illustration of the thoracic cross-sectional plane E with rasterized EIT pixels xy that is quite similar to FIG. 2d. FIG. 2e finally shows a binarized version of the impedance distribution at the end of the expiration that is already shown in FIG. 2b. Shaded in dark in FIG. 2e are those EIT pixels xy of FIG. 2b that have impedance values at the end of the expiration phase EIT_ee_xy associated therewith that are at least as great as 1.3 times of the minimum impedance EIT_ei_min occurring among all EIT pixels xy in the thoracic cross-sectional plane E at the end of the expiration phase. Shaded in light color are all remaining EIT pixels xy having impedance values at the end of the expiration phase EIT_ee_xy associated therewith which are smaller than 1.3 times the minimum impedance EIT_ei_min occurring among all EIT pixels xy in the thoracic cross-sectional plane E at the end of the expiration phase. This is expressed in a formula as follows:

EIT pixels xy are shaded in dark color in FIG. 2e when the following holds:
$$EIT\_ee\_xy \geq 1.3 * EIT\_ee\_min,$$
EIT pixels xy are shaded in light color in FIG. 2e when the following holds:
$$EIT\_ei\_xy < 1.3 * EIT\_ee\_min,$$
wherein: $EIT\_ee\_min = min(EIT\_ee\_xy;$ for all possible xy)

It can be seen in FIG. 2e that, at the end of expiration, there is a tendency for higher breathing gas pressures remaining in a central region 48a, 48b of the two lobes 40a, 40b than in a peripheral region 50a, 50b. FIG. 2c nevertheless shows that in all regions of the lungs 40 the difference between the impedance at the end of inspiration and the impedance at the end of expiration is clearly higher than the selected threshold value, which indicates that the alveoli in all regions of the lungs participate normally in the gas exchange.

The conditions shown for healthy lungs with regard to FIGS. 2a to 2e are different in case of lungs the alveoli of which have partly collapsed during expiration due to the application of a too low PEEP, cf. FIGS. 3a to 3e, or in case of lungs the alveoli of which have been overextended during inspiration due to the application of an excessively high breathing gas pressure, cf. FIGS. 4a to 4e. The illustration shown in FIGS. 3a to 3e and FIGS. 4a to 4e respectively correspond to the illustrations in FIGS. 2a to 2e, however for lungs with party collapsed alveoli during expiration and lungs with partly overextended alveoli during inspiration, respectively. The same reference numerals are used in all figures as in FIGS. 2a to 2e, and reference is made to the respective description of the designated elements relating to FIGS. 2a to 2e for avoiding repetitions.

As in case of healthy lungs, it can be seen that also for the lungs with partly collapsed alveoli (FIGS. 3a and 3b) and for the lungs with partly overextended alveoli (FIGS. 4a and 4b) the impedance values at the end of inspiration are generally higher than at the end of expiration.

Figure 3A:
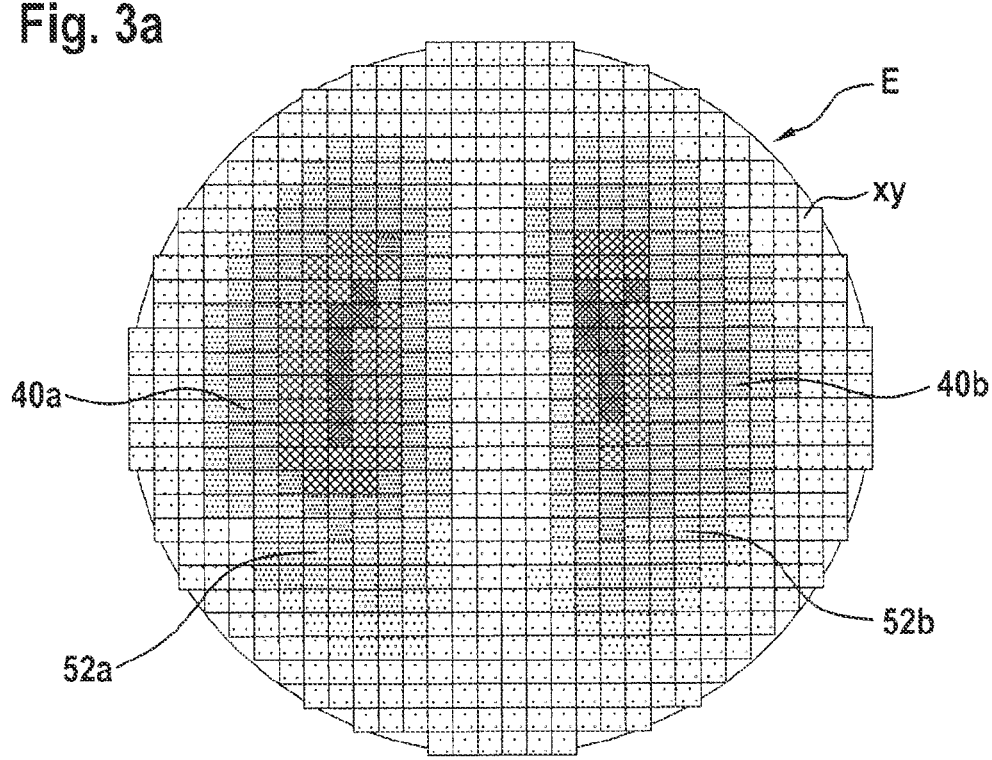
Figure 3B:
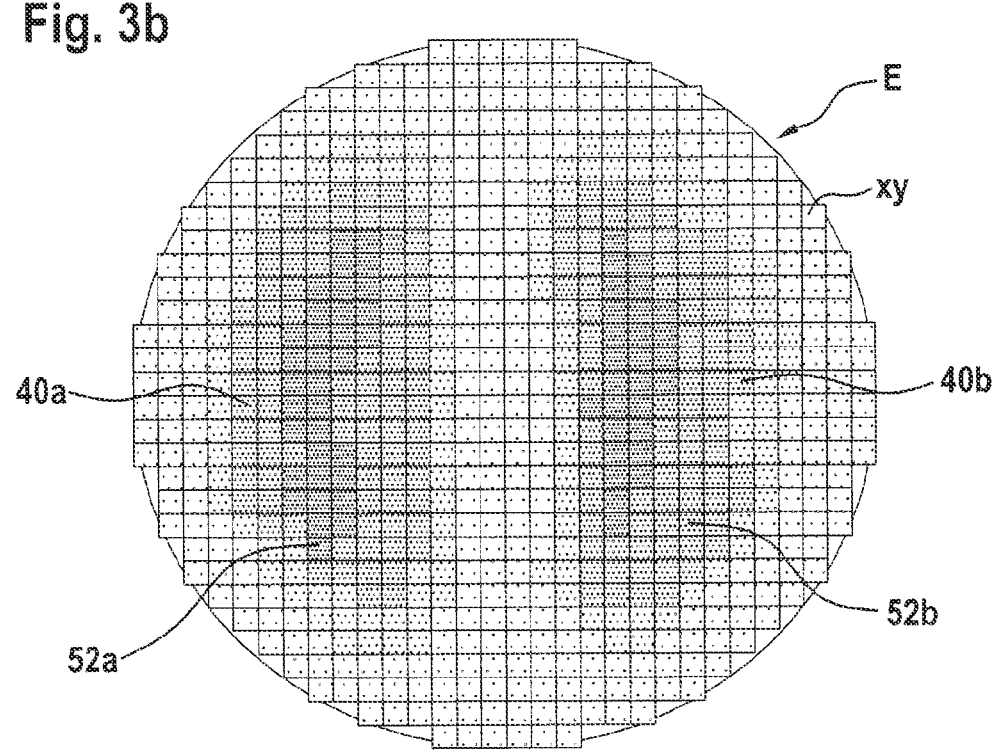
Figure 3C:
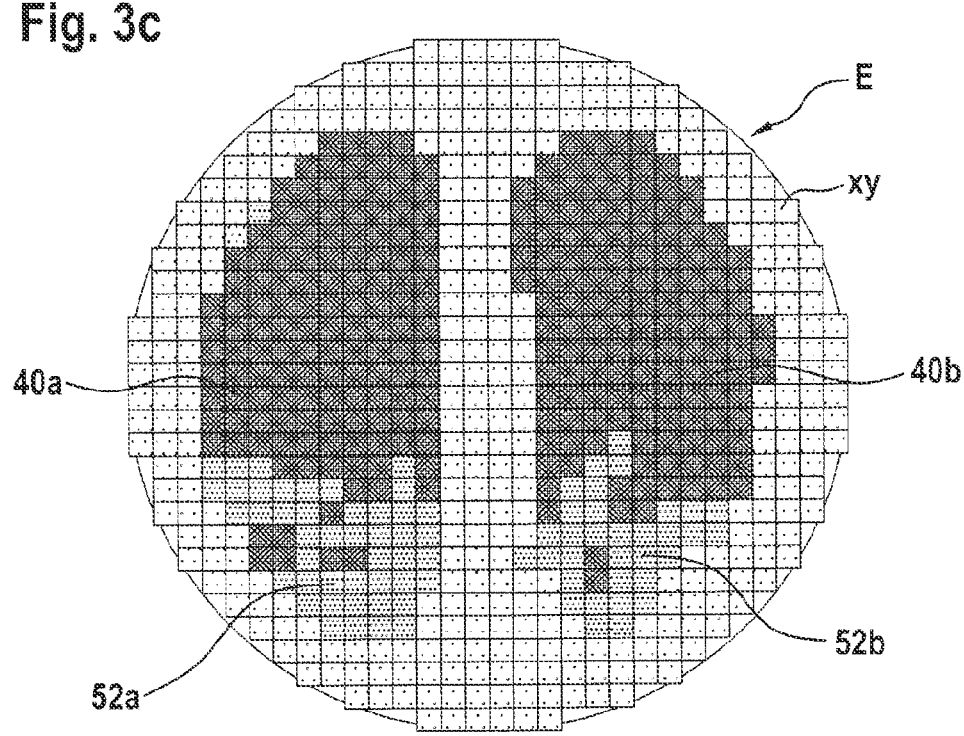
Figure 3D:
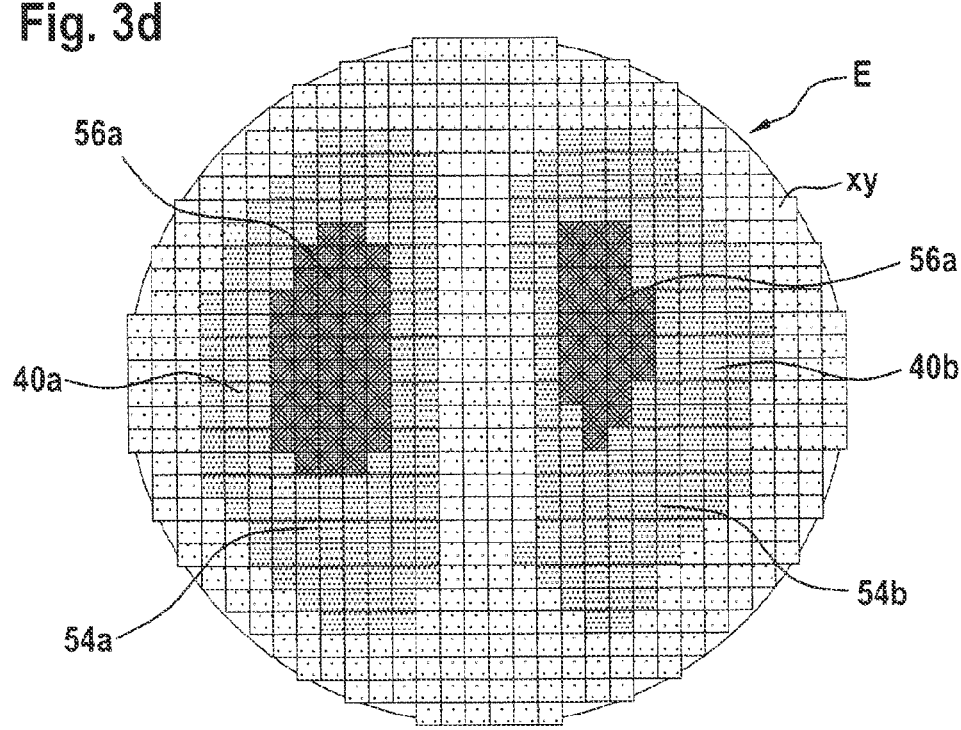

However, it is already indicated in FIGS. 3a and 3b that in the lower central region 52a, 52b of both lobes 40a, 40b of the lungs the impedance values both at the end of expiration and at the end of inspiration are slightly lower than in case of the healthy lungs illustrated in FIGS. 2a and 2b. When looking at the image of the impedance differences EIT_ei_xy−EIT_ee_xy shown in FIG. 3c, it is immediately apparent that in the lower central regions 52a, 52b of both lobes of the lungs the impedance difference is below the selected threshold value (which in the example chosen is 0.5 times the maximum impedance difference). This is a hint to the effect that the alveoli in this region are only slightly more filled with breathing gas at the end of the inspiration phase than at the end of the expiration phase.

Figure 4A:
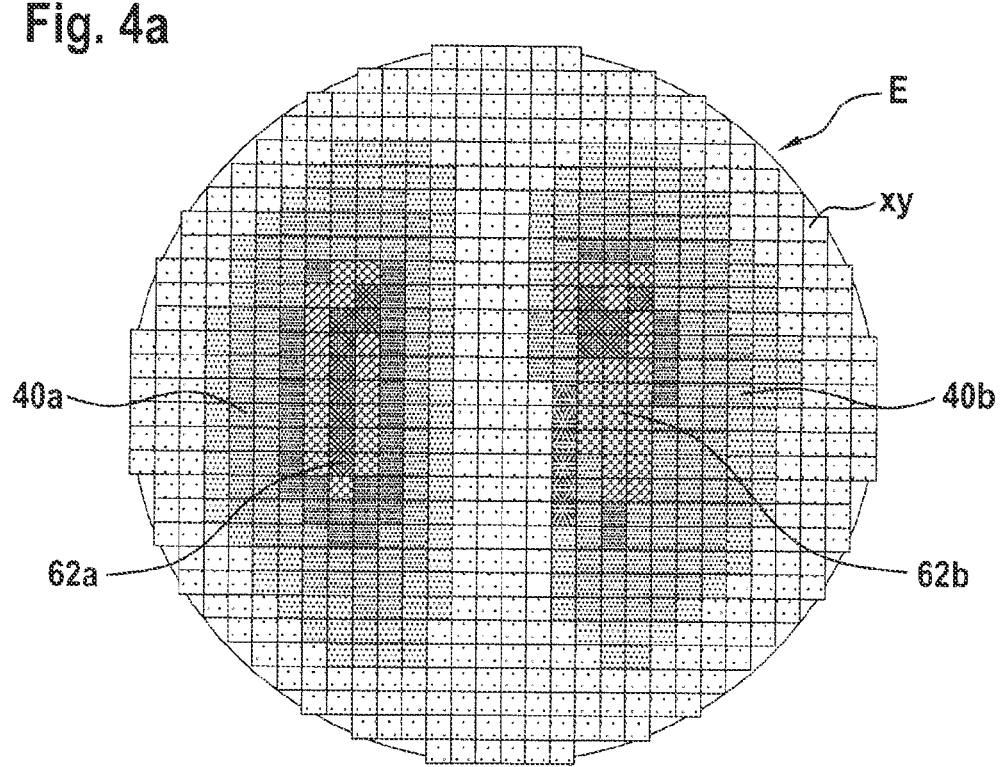
FIGS. 4a to 4e show illustrations corresponding to FIGS. 2a to 2e, however for lungs with overextended alveoli during the inspiration phase.
Figure 4B:
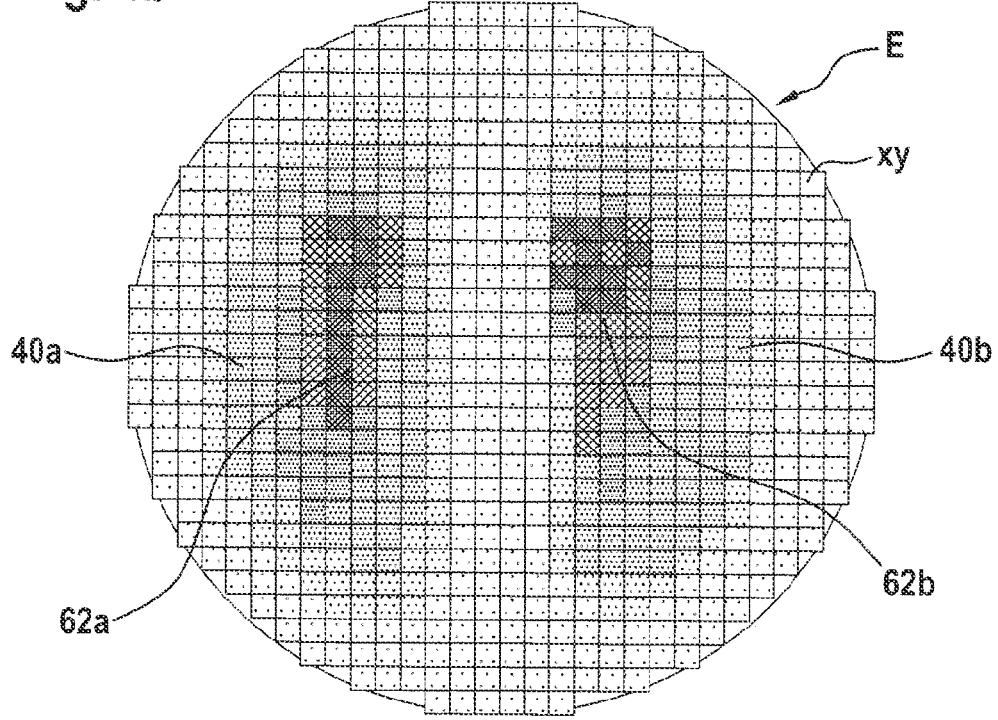
Figure 4C:
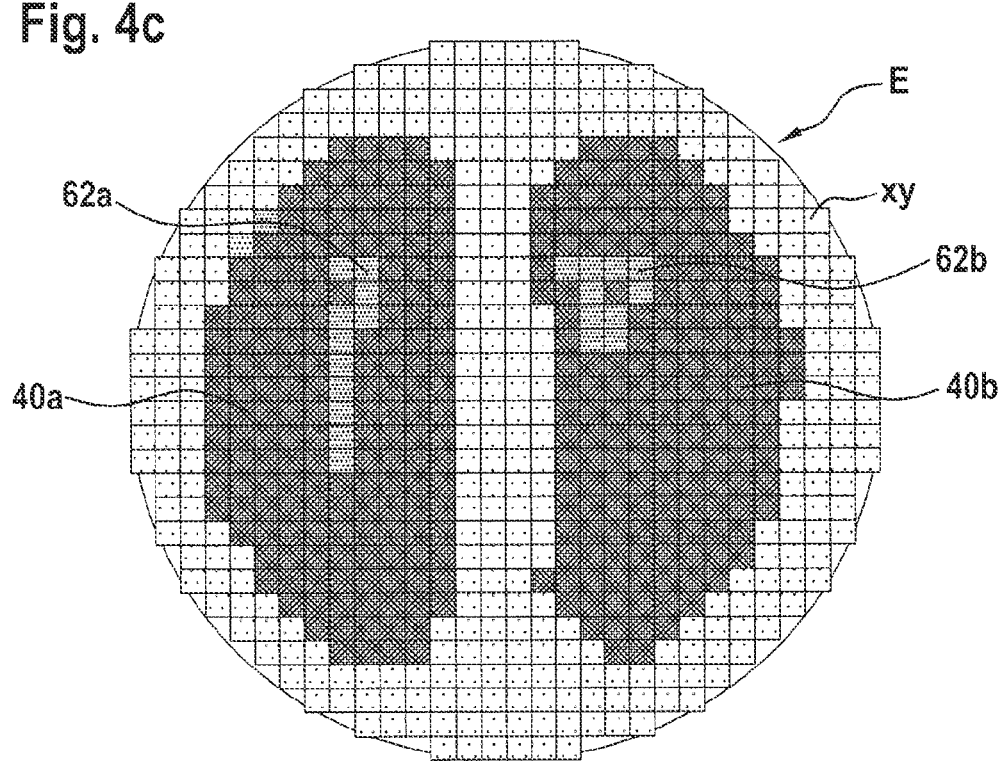
Figure 4D:
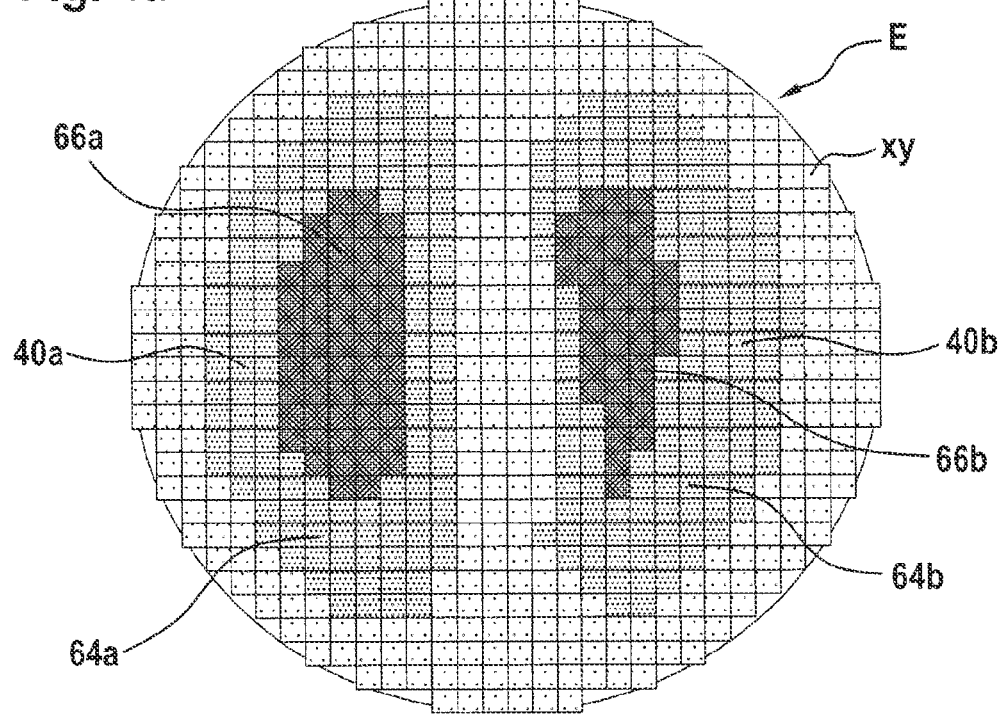
Figure 4E:
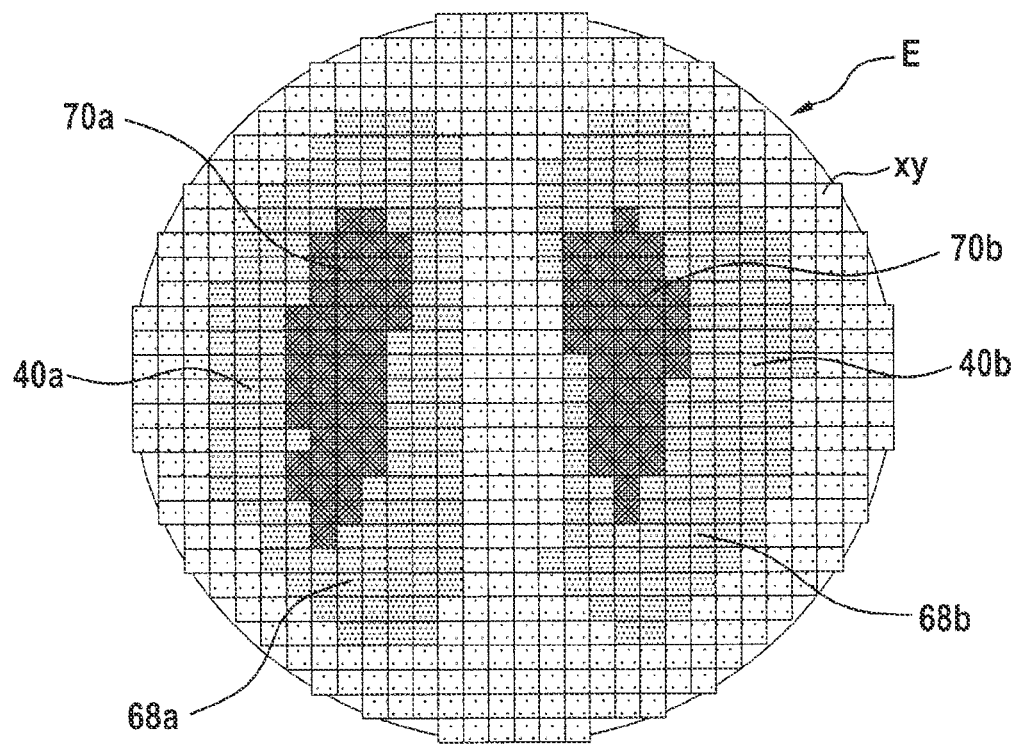

It can be guessed in FIGS. 4a and 4b that, in the central regions 62a, 62b of both lobes 40a, 40b, the impedance values both at the end of expiration and at the end of inspiration are slightly higher than in the healthy lungs illustrated in FIGS. 2a and 2b. When looking at the image of the impedance differences EIT_ei_xy−EIT_ee_xy shown in FIG. 4c, it is immediately apparent that, here too, the impedance difference in the central regions 62a, 62b of both lobes 40a, 40b of the lungs is below the selected threshold value (which in the example chosen is 0.5 times the maximum impedance difference). This is a hint to the effect that the alveoli in this region are filled in similar manner with breathing gas both at the end of the inspiration phase and at the end of the expiration phase.

Thus, by way of an evaluation of the difference between the impedance at the end of the inspiration phase EIT_ei_xy and the impedance at the end of the expiration phase EIT_ee_xy, a distinction can be made for each EIT pixel xy whether the alveoli associated with this EIT pixel xy are substantially healthy or subject to a pathological change. This distinction even can be made when the lungs, for one and the same breathing cycle, have both regions with overextended alveoli and regions with collapsed alveoli, as in both cases (cf. FIGS. 3c and 4c) the same threshold value can be used for distinction. However, it is not possible to make a distinction as to whether the alveoli in the pathological regions 52a, 52b, 62a, 62b have collapsed during the expiration phase or have been overextended during the inspiration phase.

However, when looking at the binarized values of the impedances in the thoracic cross-sectional plane E at the end of the inspiration phase and at the end of the expiration phase, respectively, as shown in FIGS. 3d, 3e and FIGS. 4d, 4e, the following can be seen:

For EIT pixels xy in regions 52a, 52b of the lobes of the lungs with alveoli having collapsed during the expiration phase, the impedance values at the end of expiration EIT_ee_xy are low as well. This can be seen in FIG. 3e from the fact that all of these EIT pixels belong to the regions 58a, 58b shaded in light color, and thus have impedance values that are located within a quite narrow restricted region around the minimum impedance value at the end of expiration. From this follows: all EIT pixels xy that are shaded in light color both in the binarized illustration of the impedance differences EIT_ei_xy–EIT_ee_xy according to FIG. 3c and in the binarized illustration of the impedances at the end of expiration EIT_ee_xy according to FIG. 3e, have collapsed alveoli to a considerable extent. Both criteria can be examined quite easily in an automated respiration system so that it is possible to recognize without human intervention whether the setting chosen for the respiration parameters needs to be corrected since alveoli collapse during expiration in parts of the lungs. In such cases, it may be provided, for example, that the respiration system automatically adjusts a slightly higher PEEP.

For EIT pixels xy in the regions 62a, 62b of the lobes of the lungs, containing alveoli that have been overextended during the inspiration phase, the impedance values at the end of inspiration EIT_ei_xy are high as well. This can be seen in FIG. 4d from the fact that all of these EIT pixels belong to the regions 66a, 66b shaded in dark color, and thus have impedance values that are located in a quite narrow restricted area around the maximum impedance value at the end of inspiration. From this follows: all of the EIT pixels xy which both in the binarized illustration of the impedance differences EIT_ei_xy–EIT_ee_xy are shaded in light color according to FIG. 3c and in the binarized illustration of the impedance values at the end of inspiration EIT_ei_xy are shaded in dark color according to FIG. 4d, have overextended alveoli to a considerable extent. Also these two criteria can be examined quite easily in an automated respiration system so that it is possible to recognize without human intervention whether the adjustment chosen for the respiration parameters needs to be corrected since alveoli have been overextended during inspiration in parts of the lungs. In such cases, it may be provided, for example, that the respiration system automatically adjusts a slightly lower maximum respiration pressure Paw_max.

In situations in which, during one and the same breathing cycle, there are both regions in the lungs in which alveoli are overextended during the inspiration phase, as well as regions in the lungs in which alveoli collapse during the expiration phase, it is also easily possible to make a distinction between such regions by the mutually separate examination of the two afore-mentioned cumulative conditions. As a consequence of the occurrence of lung regions with overextended alveoli and lung regions with collapsed alveoli, the PEEP will be increased on the one hand, in order to counteract the collapsing of alveoli, and the maximum airway pressure will also be reduced on the other hand, in order to counteract the overextension of alveoli. This is accompanied by a corresponding reduction of the tidal pressure in the subsequent breathing cycles. This too can be implemented in an automatically operating procedure.

The present invention thus provides the possibility of a largely automatically operating respiration device that is capable of adjusting essential respiration pressures, such as the PEEP and/or the maximum respiration pressure, without intervention by physicians or nursing staff when there is a change in physiological parameters.

Adjustment or tracking of the PEEP, for example, can be effected in that, starting from a relatively low initial value for the PEEP, the respective EIT data recorded after each breathing cycle or after a predetermined number of breathing cycles are evaluated in the manner described hereinbefore, and the percentage of EIT pixels xy is determined for which both of the afore-mentioned criteria are present, i.e., for which holds:

EIT_ei_xy − EIT_ee_xy < k1 * max(EIT_ei_xy − EIT_ee_xy;
    for all possible xy)
AND
EIT_ee_xy < k2 * min(EIT_ee_xy; for all possible xy)
wherein:
  EIT_ei_xy:  electrical impedance value at the end of the inspiration phase associated with a respective EIT pixel
  EIT_ee_xy:  electrical impedance value at the end of the expiration phase associated with a respective EIT pixel,
  0 ≤ k1 ≤ 1,  in particular 0.3 ≤ k1 ≤ 0.7,
    in particular 0.4 ≤ k1 ≤ 0.6,
    in particular k1 = 0.5;
  k2 ≥ 1,  in particular 1.0 ≤ k2 ≤ 1.6,
    in particular 1.2 ≤ k2 ≤ 1.4,
    in particular k2 = 1.3.

When the percentage of EIT pixels xy for which the comparison is positive in the total number of EIT pixels xy exceeds a predetermined first threshold value k5, the respiration device increases the value of the PEEP for the subsequent breathing cycles by a predetermined amount. The first threshold value k5, for example, can be in a range from 5 to 25%, and in particular may be 10%. The PEEP can be increased by 1 cm $H_2O$ each, for example, when the first threshold value k5 is exceeded. As starting value for the PEEP, it is advisable to use a moderate value which still leaves upward leeway for adjustment, for example 10 cm $H_2O$.

This comparison then this repeated in predetermined time intervals. The PEEP for the respective subsequent breathing cycles is increased as long as the percentage of EIT pixels xy for which the comparison is positive in the total number of the EIT pixels xy is below the first threshold value k5. Also following this, the comparison is repeated in predetermined time intervals. As long as the percentage of EIT pixels for which the comparison is positive, is below the first threshold value k5, the PEEP remains unchanged. If one of the comparisons again results in a percentage of EIT pixels xy for which the comparison is positive that corresponds to the threshold value k5 or is greater than the same, the PEEP is increased again.

The value of the first threshold value k5 can be selected higher with an increasing value of the set PEEP. By doing so, it is prevented that the respiration system continues to increase the PEEP when the percentage of EIT pixels xy with collapsed alveoli does not change in response to an increase of the PEEP. In the above-mentioned example of increasing the PEEP by 1 cm H$_2$O per step starting from in an initial value of 10 cm H$_2$O for the PEEP, it is possible for example to increase the value of the first threshold value k5 in each increase of the PEEP by 0.3 to 3%, in particular by 1%.

For automated adjustment or tracking of a maximum airway pressure Paw_max, it is possible for example that, starting from a relatively high initial value for the maximum airway pressure Paw_max, after each breathing cycle or after a predetermined number of breathing cycles, respectively, the respective EIT data recorded are evaluated in the manner described hereinbefore and the percentage of EIT pixels xy is determined for which the following two conditions are fulfilled:

---

EIT_ei_xy − EIT_ee_xy < k3 * max(EIT_ei_xy − EIT_ee_xy;
                for all possible xy)
                AND
EIT_ei_xy > k4 * max(EIT_ei_xy; for all possible xy)
wherein:
   EIT_ei_xy:   electrical impedance value at the end of the inspiration phase associated with a respective EIT pixel
   EIT_ee_xy:   electrical impedance at the end of the expiration phase associated with a respective EIT pixel,
   0 ≤ k3 ≤ 1,   in particular 0.3 ≤ k3 ≤ 0.7,
                  in particular 0.4 ≤ k3 ≤ 0.6,
                  in particular k3 = 0.5;
   0 ≤ k4 ≤ 1,   in particular 0.5 ≤ k4 ≤ 0.9,
                  in particular 0.6 ≤ k4 ≤ 0.8,
                  in particular k4 = 0.7.

---

When the percentage of EIT pixels xy for which the comparison is positive in the total number of EIT pixels xy exceeds a predetermined second threshold value k6, the respiration device decreases the value of the maximum airway pressure Paw_max for the subsequent breathing cycles by a predetermined amount. The first threshold value k6, for example, can be in a range from 5 to 25%, and in particular may be 10%. The maximum airway pressure Paw_max can be decreased by 1 cm H$_2$O each, for example, when the second threshold value k6 is exceeded. As starting value for the maximum airway pressure Paw_max, it is advisable to use a rather high value, for example 40 cm H$_2$O.

This comparison then this repeated in predetermined time intervals. The maximum airway pressure Paw_max for the respective subsequent breathing cycles is decreased as long as the percentage of EIT pixels xy for which the comparison is positive in the total number of the EIT pixels xy is below the second threshold value k6. Also following this, the comparison is repeated in predetermined time intervals. As long as the percentage of EIT pixels for which the comparison is positive is below the second threshold value k6, the airway pressure Paw_max remains unchanged. If one of the comparisons again results in a percentage of EIT pixels xy for which the comparison is positive that corresponds to the threshold value k6 or is greater than the same, the airway pressure Paw_max is decreased again.

The value of the second threshold value k6 can be selected higher with a decreasing value of the set maximum airway pressure Paw_max. By doing so, it is prevented that the respiration system continues to decrease the maximum airway pressure Paw_max when the percentage of EIT pixels xy with overextended alveoli does not change in response to a decrease of the maximum airway pressure Paw_max. In the above-mentioned example of decreasing the maximum airway pressure Paw_max by 1 cm H$_2$O per step starting from in an initial value of 40 cm H$_2$O for the maximum airway pressure Paw_max, it is possible for example to increase the value of the second threshold value k6 with each decrease of Paw_max by 0.3 to 3%, in particular by 1%.

The invention claimed is:

1. A system for automated adjustment of a pressure set by a respiration device, the system comprising:
   an arrangement for electrical impedance tomography for detecting electrical impedance distributions along at least a two-dimensional cross-section through a human thorax at least at an end of an inspiration phase and at an end of an associated expiration phase;
   a device for dividing the detected electrical impedance distributions at the end of the inspiration phase and at the end of the expiration phase into a plurality of EIT pixels and for determining a value of the electrical impedance at the end of the inspiration phase and a value of the detected electrical impedance at the end of the expiration phase, as associated with a respective EIT pixel; and
   a device for automated adjustment of a pressure set by the respiration device based on a comparison:
   (i) of a deviation between the value of the electrical impedance at the end of the inspiration phase associated with an individual EIT pixel and the value of the electrical impedance at the end of the expiration phase associated with the respective EIT pixel,
   (ii) with a deviation between the value of the electrical impedance at the end of the inspiration phase and the value of the electrical impedance at the end of the expiration phase, as determined based on the entirety of the EIT pixels.

2. The system of claim 1, wherein the deviation between the value of the electrical impedance at the end of the inspiration phase associated with an individual EIT pixel and the value of the electrical impedance at the end of the expiration phase associated with the respective individual EIT pixel and/or the deviation between the value of the electrical impedance at the end of the inspiration phase and the value of the electrical impedance at the end of the expiration phase, as determined based on the entirety of the EIT pixels, is defined as a difference between the respective values of the electrical impedance at the end of the inspiration phase and the electrical impedance at the end of the expiration phase.

3. The system of claim 1, wherein the deviation between the value of the electrical impedance at the end of the inspiration phase associated with an individual EIT pixel and the value of the electrical impedance at the end of the expiration phase associated with the respective individual EIT pixel and/or the deviation between the value of the electrical impedance at the end of the inspiration phase and the value of the electrical impedance at the end of the expiration phase, as determined based on the entirety of the EIT pixels, is defined as a ratio between the respective values of the electrical impedance at the end of the inspiration phase and the electrical impedance at the end of the expiration phase.

4. The system of claim 1, wherein the deviation between the value of the electrical impedance at the end of the inspiration phase and the value of the electrical impedance at the end of the expiration phase, as determined based on the entirety of the EIT pixels, is a maximum value of all differences between the values of the electrical impedance at the end of the inspiration phase for respective ones of the EIT pixels and the values of the electrical impedance at the end of the expiration phase for said respective ones of the EIT pixels.

5. The system of claim 1, wherein the device for automated adjustment of the pressure set by the respiration device compares the deviation between the value of the electrical impedance at the end of the inspiration phase and the value of the electrical impedance at the end of the expiration phase, as associated with a respective EIT pixel also with the value of the electrical impedance at the end of the inspiration phase and/or at the end of the expiration phase, as respectively determined based on the entirety of the EIT pixels.

6. The system of claim 1, wherein the device for automated adjustment of the pressure set by the respiration device determines the EIT pixels that fulfill a predetermined condition, and effects a correction of the set pressure when a percentage of EIT pixels fulfilling said condition is greater than a predetermined threshold value.

7. The system of claim 1, comprising a device for automated adjustment of a positive end-expiratory pressure set by the respiration device based on a comparison:
   (i) of a deviation between the value of the electrical impedance at the end of the inspiration phase associated with an individual EIT pixel and the value of the electrical impedance at the end of the expiration phase associated with the respective individual EIT pixel,
   (ii) with a deviation between the value of the electrical impedance at the end of the inspiration phase and the value of the electrical impedance at the end of the expiration phase, as determined based on the entirety of the EIT pixels, and the value of the electrical impedance at the end of the expiration phase as determined based on the entirety of the EIT pixels.

8. The system of claim 7, wherein the value of the electrical impedance at the end of the expiration phase determined based on the entirety of the EIT pixels is a minimum value of all values of the electrical impedance at the end of the expiration phase for respective ones of the EIT pixels.

9. The system of claim 7, wherein the device for automated adjustment of a positive end-expiratory pressure set by the respiration device associates the EIT pixels for which the comparison is positive with lung regions having collapsed alveoli.

10. The system of claim 9, wherein the association of EIT pixels with lung regions with collapsed alveoli is effected when the following two conditions are fulfilled:

$$EIT\_ei\_xy - EIT\_ee\_xy < k1 * \max(EIT\_ei\_xy - EIT\_ee\_xy;$$
$$\text{for all possible xy})$$
$$\text{AND}$$
$$EIT\_ee\_xy < k2 * \min(EIT\_ee\_xy; \text{for all possible xy})$$

wherein:
- $EIT\_ei\_xy$: electrical impedance value at the end of the inspiration phase associated with a respective EIT pixel,
- $EIT\_ee\_xy$: electrical impedance value at the end of the expiration phase associated with a respective EIT pixel,
- $0 \le k1 \le 1$, and
- $k2 \ge 1$.

11. The system of claim 7, wherein the device for automated adjustment of a positive end-expiratory pressure set by the respiration device increases a value of the positive end-expiratory pressure for the subsequent breathing cycles by a predetermined amount, when a percentage of EIT pixels, for which the comparison is positive, exceeds a predetermined first threshold value in a total number of EIT pixels.

12. The system of claim 7, wherein the comparison is repeated at predetermined time intervals and the positive end-expiratory pressure for the subsequent breathing cycles is increased until a percentage of EIT pixels, for which the comparison is positive, in a total number of EIT pixels, is below the first threshold value.

13. The system of claim 11, wherein the first threshold value is selected greater with an increasing value of the positive end-expiratory pressure.

14. The system of claim 1, comprising a device for automated adjustment of a maximum airway pressure set by the respiration device, based on a comparison:
   (i) of a deviation between the value of the electrical impedance at the end of the inspiration phase associated with an individual EIT pixel and the value of the electrical impedance at the end of the expiration phase associated with the respective individual EIT pixel,
   (ii) with a deviation between the value of the electrical impedance at the end of the inspiration phase and the value of the electrical impedance at the end of the expiration phase, as determined based on the entirety of the EIT pixels, and the value of the electrical impedance at the end of the inspiration phase, as determined based on the entirety of the EIT pixels.

15. The system of claim 14, wherein the value of the electrical impedance at the end of the inspiration phase, as determined based on the entirety of the EIT pixels, is a maximum value of all values of the electrical impedance at the end of the inspiration phase for respective ones of the EIT pixels.

16. The system of claim 14, wherein the device for automated adjustment of a maximum airway pressure set by the respiration device associates those EIT pixels for which the comparison is positive with lung regions having overextended alveoli.

17. The system of claim 16, wherein the association of EIT pixels with lung regions having overextended alveoli is effected when the following two conditions are fulfilled:

$$EIT\_ei\_xy - EIT\_ee\_xy < k3 * \max(EIT\_ei\_xy - EIT\_ee\_xy;$$
$$\text{for all possible xy})$$
$$\text{AND}$$
$$EIT\_ei\_xy > k4 * \max(EIT\_ei\_xy; \text{for all possible xy})$$

wherein:
- $EIT\_ei\_xy$: electrical impedance value at the end of the inspiration phase associated with a respective EIT pixel,
- $EIT\_ee\_xy$: electrical impedance value at the end of the expiration phase associated with a respective EIT pixel,
- $0 \le k3 \le 1$, and
- $0 \le k4 \le 1$.

18. The system of claim 14, wherein the device for automated adjustment of a maximum airway pressure set by the respiration device decreases the value of the maximum airway pressure for the subsequent breathing cycles by a predetermined amount, when a percentage of EIT pixels, for which the comparison is positive, exceeds a predetermined second threshold value in a total number of EIT pixels.

19. The system of claim 14, wherein the comparison is repeated in predetermined time intervals and the maximum airway pressure for the subsequent breathing cycles is decreased until a percentage of EIT pixels, for which the comparison is positive, in the total number of EIT pixels, is below the second threshold value.

20. The system of claim 18, wherein the value of the second threshold value is selected greater with a decreasing value of the maximum airway pressure.

21. The system of claim 1, wherein the arrangement for electrical impedance tomography detects an electrical impedance distribution in a form of electrical impedance values associated with EIT pixels arranged in a predetermined grid, and wherein the device for dividing the detected electrical impedance distribution into a plurality of EIT pixels associates exactly a respective value of the electrical impedance with a respective grid element.

22. The system of claim 1, wherein the arrangement for electrical impedance tomography detects an electrical impedance distribution in a form of electrical impedance values associated with elementary EIT pixels arranged in a predetermined grid, and wherein the device for dividing the detected electrical impedance distribution into a plurality of EIT pixels associates a respective one of the EIT elementary pixels with exactly one EIT pixel and determines for each one of the EIT pixels an associated value of the electrical impedance.

23. The system of claim 1, further comprising a filter device for filtering out such rapidly time-variable components from the detected electrical impedance values that are due to cardiac effects.

24. A respiration device, comprising:
a system for automatic adjustment of a pressure set by the respiration device, the system including:
an arrangement for electrical impedance tomography for detecting electrical impedance distributions along at least a two-dimensional cross-section through a human thorax at least at an end of an inspiration phase and at an end of an associated expiration phase;
a device for dividing the detected electrical impedance distributions at the end of the inspiration phase and at the end of the expiration phase into a plurality of EIT pixels and for determining a value of the electrical impedance at the end of the inspiration phase and a value of the detected electrical impedance at the end of the expiration phase, as associated with a respective EIT pixel; and
a device for automated adjustment of a pressure set by the respiration device based on a comparison:
(i) of a deviation between the value of the electrical impedance at the end of the inspiration phase associated with an individual EIT pixel and the value of the electrical impedance at the end of the expiration phase associated with the respective EIT pixel,
(ii) with a deviation between the value of the electrical impedance at the end of the inspiration phase and the value of the electrical impedance at the end of the expiration phase, as determined based on an entirety of the EIT pixels.

25. A method for automated adjustment of a pressure set by a respiration device, in particular a positive end-expiratory pressure and a maximum airway pressure, the method comprising:
with the aid of an arrangement for electrical impedance tomography, detecting an electrical impedance distribution along at least a two-dimensional cross-section through a human thorax at least at the end of an inspiration phase and at the end of an associated expiration phase,
dividing the detected electrical impedance distribution at the end of the inspiration phase and at the end of the expiration phase into a plurality of EIT pixels;
associating a respective value of the electrical impedance at the end of the inspiration phase and at the end of the expiration phase with each one of the EIT pixels, and
determining the pressure set by the respiration device based on a comparison:
(i) of a deviation between the value of the electrical impedance at the end of the inspiration phase associated with an individual EIT pixel and the value of the electrical impedance at the end of the expiration phase associated with a respective individual EIT pixel,
(ii) with a deviation between the value of the electrical impedance at the end of the inspiration phase and the value of the electrical impedance at the end of the expiration phase, as determined based on an entirety of the EIT pixels.

* * * * *